US007655446B2

(12) United States Patent
Jacobs et al.

(10) Patent No.: US 7,655,446 B2
(45) Date of Patent: Feb. 2, 2010

(54) CRYSTAL STRUCTURE OF RHO-KINASE I KINASE DOMAIN COMPLEXES AND BINDING POCKETS THEREOF

(75) Inventors: Marc Jacobs, Boston, MA (US); Koto Hayakawa, Edmonton (CA); Mark Fleming, Cambridge, MA (US); John Doran, Medford, MA (US); Craig Marhefka, Rockville, MD (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/478,194

(22) Filed: Jun. 28, 2006

(65) Prior Publication Data

US 2009/0036654 A1 Feb. 5, 2009

Related U.S. Application Data

(60) Provisional application No. 60/695,161, filed on Jun. 28, 2005.

(51) Int. Cl.
*C12N 9/00* (2006.01)
*G01N 31/00* (2006.01)
(52) U.S. Cl. .......................................... 435/183; 436/4
(58) Field of Classification Search ........................ None
See application file for complete search history.

(56) References Cited

U.S. PATENT DOCUMENTS

| 4,886,646 | A | 12/1989 | Carter et al. |
|---|---|---|---|
| 5,096,676 | A | 3/1992 | McPherson et al. |
| 5,130,105 | A | 7/1992 | Carter et al. |
| 5,221,410 | A | 6/1993 | Kushner et al. |
| 5,400,741 | A | 3/1995 | DeTitta et al. |
| 5,884,230 | A | 3/1999 | Srinivasan et al. |

OTHER PUBLICATIONS

McPherson Eur. J. Biochem. 1990, 189:1-23.*
Kundrot et al. Cell. Mol. Life Sci. 2004, 61: 525-536.*
Benevenuti et al., Nature Protocols, published on-line Jun. 28, 2007, 2(7):1633-1651.*
R. Cudney, Rigaku Journal, 1999, vol. 16, No. 1, pp. 1-7.*
Drenth, "Principles of Protein X-Ray Crystallography", 2nd Edition, 1999 Springer-Verlag New York Inc., Chapter 1, p. 19, 4th paragraph, lines 1-2.*
Amano et al., "Phosphorylation and Activation of Myosin by Rho-associated Kinase (Rho-Kinase)," *The Journal of Biological Chemistry*, 271(34):20246-20249 (1996).
Amano et al., "Myosin II Activation Promotes Neurite Retraction during the Action of Rho and Rho-kinase," *Genes to Cells*, 3:177-188 (1998).
Amano et al., The COOH Terminus of Rho-Kinase Negatively Regulates Rho-Kinase Activity, *The Journal of Biological Chemistry*, 274(45):32418-32424 (1999).

Balbes et al., "A Perspective of Modern Methods in Computer-Aided Drug Design," *Reviews in Computational Chemistry*, K.B. Lipkowitz and D.B. Boyd Eds., VCH Publishers, New York, 5:337-379 (1994).
Bartlett et al., "CAVEAT: A Program to Facilitate the Structure-derived Design of Biologically Active Molecules," *Molecular Recognition in Chemical and Biological Problems*, S.M. Roberts, Ed., Royal Society of Chemistry, 78:182-196 (1989).
Blundell et al., "Knowledge-based Prediction of Protein Structures and the Design of Novel Molecules," *Nature*, 326:347-352 (1987).
Böhm, "The Computer Program LUDI: A New Method for the *de novo* Design of Enzyme Inhibitors," *Journal of Computer-Aided Molecular Design*, 6:61-78 (1992).
Breitenlechner et al., "Protein Kinase A in Complex with Rho-Kinase Inhibitors Y-27632, Fasudil, and H-1152P: Structural Basis of Selectivity," *Structure*, 11:1595-1607 (2003).
Brünger et al., "Crystallography & NMR System: A New Software Suite for Macromolecular Structure Determination," *Acta Crystallographica*, D54:905-921, (1998).
Carson, "Ribbons 2.0," *Journal of Applied Crystallography*, 24:958-961 (1991).
Chambers et al., "High-throughput Screening for Soluble Recombinant Expressed Kinases in *Escherichia coli* and Insect Cells," *Protein Expression and Purification*, 36:40-47 (2004).
Chayen, "A Novel Technique to Control the Rate of Vapour Diffusion, Giving Larger Protein Crystals," *Journal of Applied Crystallography*, 30:198-202 (1997).
Cohen et al., "Molecular Modeling Software and Methods for Medicinal Chemistry," *Journal of Medicinal Chemistry*, 33(3):883-894 (1990).
Cory and Bentley, "MATCHMOL, an Interactive Computer Graphics Procedure for Superposition of Molecular Models," *Journal of Molecular Graphics*, 2:39-42 (1984).
D'Arcy et al., "A Novel Approach to Crystallising Proteins under Oil," *Journal of Crystal Growth*, 168:175-180 (1996).
Dayhoff et al., "A Model of Evolutionary Change in Proteins," *Atlas of Protein Sequence and Structure*, 5(3):345-352 (1978).
Doran et al., "New Insights into the Structure-Function Relationships of Rho-associated Kinasâ: A Thermodynamic and Hydrodynamic Study of the Dimer-to-Monomer Transition and its Kinetic Implications," *Biochemical Journal*, 384:255-262 (2004).

(Continued)

*Primary Examiner*—Suzanne M. Noakes
(74) *Attorney, Agent, or Firm*—Ropes & Gray LLP; James F. Haley, Jr.; Raymond M. Doss

(57) ABSTRACT

The present invention relates to human Rho-kinase I (ROCK I), ROCK I binding pockets, ROCK I-like binding pockets. More particularly, the present invention provides a computer comprising a data storage medium encoded with the structure coordinates of such binding pockets. This invention also relates to methods of using the structure coordinates to solve the structure of homologous proteins or protein complexes. In addition, this invention relates to methods of using the structure coordinates to screen for and design compounds, including inhibitory compounds, that bind to ROCK I protein or ROCK I protein homologues, or complexes thereof. The invention also relates to crystallizable compositions and crystals comprising ROCK I kinase domain and ROCK I kinase domain complexed with an inhibitor of that domain. The invention also relates to methods of identifying inhibitors of the ROCK I kinase domain.

2 Claims, 7 Drawing Sheets

OTHER PUBLICATIONS

Eisen et al., "HOOK: A Program for Finding Novel Molecular Architectures that Satisfy the Chemical and Steric Requirements of a Macromolecule Binding Site," *Proteins: Structure, Functions and Genetics*, 19:199-221 (1994).

Fetrow and Bryant, "New Programs for Protein Tertiary Structure Prediction," *Bio/Technology*, 11:479-484 (1993).

Fox et al., "A Single Amino Acid Substitution Makes ERK2 Susceptible to Pyridinyl Imidazole Inhibitors of p38 MAP Kinase," *Protein Science*, 7, 2249-2255 (1998).

Gillet et al., "SPROUT: A Program for Structure Generation," *Journal of Computer-Aided Molecular Design*, 7:127-153 (1993).

Goodford, "A Computational Procedure for Determining Energetically Favorable Binding Sites on Biologically Important Macromolecules," *Journal of Medicinal Chemistry*, 28:849-857 (1985).

Goodsell and Olson, "Automated Docking of Substrates to Proteins by Simulated Annealing," *Proteins: Structure, Function and Genetics*, 8:195-202 (1990).

Greer, "Comparative Modeling of Homologous Proteins," *Methods in Enzymology*, 202:239-252 (1991).

Gschwend et al., "Molecular Docking Towards Drug Discovery," *Journal of Molecular Recognition*, 9:175-186 (1996).

Guex and Peitsch, "Swiss-Model: and the Swiss-PdbViewer: An Environment for Comparative Protein Modeling," *Electrophoresis*, 18:2714-2723 (1997).

Guida, "Software for Structured-based Drug Design," *Current Opinion in Structural Biology*, 4:777-781 (1994).

Hammond et al., "Characterization of Two Alternately Spliced Forms of Phospholipase D1," *The Journal of Biological Chemistry*, 272(6):3860-3868 (1997).

Hanks et al., "The Protein Kinase Family: Conserved Features and Deduced Phylogeny of the Catalytic Domains," *Science*, 241:42-52 (1988).

Hanks and Quinn, "Protein Kinase Catalytic Domain Sequence Database: Identification of Conserved Features of Primary Structure and Classification of Family Members," *Methods in Enzymology*, 200:38-62 (1991).

Higgins et al., "Using CLUSTAL for Multiple Sequence Alignments," *Methods in Enzymology*, 266:383-402 (1996).

Hirose et al., "Molecular Discussion of the Rho-associated Protein Kinase (p160ROCK)-regulated Neurite Remodeling in Neuroblastoma N1E-115 Cells," *The Journal of Cell Biology*, 141(7):1625-1636 (1998).

Ishizaki et al., "p160$^{ROCK}$, a Rho-associated Coiled-coil Forming Protein Kinase, Works Downstream of Rho and Induces Focal Adhesions," *FEBS Letters*, 404:118-124 (1997).

Johnson et al., "Knowledge-Based Protein Modeling," *Critical Reviews in Biochemistry and Molecular Biology*. 29:1-68 (1994).

Jones et al., "Improved Methods for Building Protein Models in Electron Density Maps and the Location of Errors in these Models," *Acta Crystallographica*, A47:110-119 (1991).

Kawano et al., "Phosphorylation of Myosin-binding Subunit (MBS) of Myosin Phosphatase by Rho-Kinase In Vivo," *The Journal of Cell Biology*, 147(5):1023-1037 (1999).

Kuntz et al., "A Geometric Approach to Macromolecule-Ligand Interactions," *The Journal of Molecular Biology*, 161:269-288 (1982).

Kureishi et al., "Rho-associated Kinase Directly Induces Smooth Muscle Contraction through Myosin Light Chain Phosphorylation," *The Journal of Biological Chemistry*, 272(19):12257-12260 (1997).

Lattman, "Use of the Rotation and Translation Functions," *Methods in Enzymology*, 115:55-77 (1985).

Lauri and Bartlett, "CAVEAT: A Program to Facilitate the Design of Organic Molecules," *Journal of Computer-Aided Molecular Design*, 8:51-66 (1994).

Martin, "3D Database Searching in Drug Design," *Journal of Medicinal Chemistry*, 35(12):2145-2154 (1992).

Meng et al., "Automated Docking with Grid-Based Energy Evaluation," *Journal of Computational Chemistry*, 13(4):505-524 (1992).

Miranker and Karplus, "Functionality Maps of Binding Sites: A Multiple Copy Simultaneous Search Method," *Proteins: Structure, Function and Genetics*, 11:29-34 (1991).

Navaza, "Implementation of Molecular Replacement in *AMoRe*," *Acta Crystallographica*, D57:1367-1372 (2001).

Navia and Murcko, "Use of Structural Information in Drug Design," *Current Opinion in Structural Biology*, 2:202-210 (1992).

Nishibata and Itai, "Automatic Creation of Drug Candidate Structures Based on Receptor Structure. Starting Point for Artificial Lead Generation," *Tetrahedron*, 47(43):8985-8990 (1991).

Pav et al., "Microtube Batch Protein Crystallization: Applications to Human Immunodeficiency Virus Type 2 (HIV-2) Protease and Human Renin," *Proteins: Structure, Function, and Genetics*, 20:98-102 (1994).

Redington, "MOLFIT: A Computer Program for Molecular Superposition," *Computers Chemical*, 16(3):217-222 (1992).

Sahai and Marshall, "Differing Modes of Tumour Cell Invasion Have Distinct Requirements for Rho/ROCK Signalling and Extracellular Proteolysis," *Nature Cell Biology*, 5(8):711-719 (2003).

Sahai and Marshall, "RHO-GTPases and Cancer," *Nature Reviews: Cancer*, 2:133-142 (2002).

Schnare et al., "Comprehensive Comparison of Structural Characteristics in Eukaryotic Cytoplasmic Large Subunit (23 S-like) Ribosomal RNA," *Journal of Molecular Biology*, 256:701-719 (1996).

Smith and Waterman, "Comparison of Biosequences," *Advances in Applied Mathematics*, 2:482-489 (1981).

Szklarz and Halpert, "Use of Homology Modeling in Conjunction with Site-Directed Mutagenesis for Analysis of Structure-Function Relationships of Mammalian Cytochromes P450," *Life Sciences*, 61(26):2507-2520 (1997).

Totsukawa et al., "Distinct Roles of ROCK (Rho-Kinase) and MLCK in Spatial Regulation of MLC Phosphorylation for Assembly of Stress Fibers and Focal Adhesions in 3T3 Fibroblasts," *The Journal of Cell Biology*, 150(4):797-806 (2000).

Wishart et al., "Constrained Multiple Sequence Alignment Using XALIGN," *CABIOS*, 10(6):687-688 (1994).

Xie et al., "Crystal Structure of JNK3: A Kinase Implicated in Neuronal Apoptosis," *Structure*, 6:983-991 (1998).

Yoshioka et al., "Small GTP-binding Protein Rho Stimulates the Actomyosin System, Leading to Invasion of Tumor Cells," *The Journal of Biological Chemistry*, 273(9):5146-5154 (1998).

"The *CCP4* Suite: Programs for Protein Crystallography," Collaborative Computational Project, No. 4, *Acta Crystallographica*, D50:760-763 (1994).

\* cited by examiner

```
                              SEQUENCE LISTING

<160> NUMBER OF SEQ ID NOS: 5

<210> SEQ ID NO 1
<211> LENGTH: 1354
<212> TYPE: PRT
<213> ORGANISM: Homo sapiens

<400> SEQUENCE: 1

Met Ser Thr Gly Asp Ser Phe Glu Thr Arg Phe Glu Lys Met Asp Asn
 1               5                  10                  15

Leu Leu Arg Asp Pro Lys Ser Glu Val Asn Ser Asp Cys Leu Leu Asp
            20                  25                  30

Gly Leu Asp Ala Leu Val Tyr Asp Leu Asp Phe Pro Ala Leu Arg Lys
        35                  40                  45

Asn Lys Asn Ile Asp Asn Phe Leu Ser Arg Tyr Lys Asp Thr Ile Asn
    50                  55                  60

Lys Ile Arg Asp Leu Arg Met Lys Ala Glu Asp Tyr Glu Val Val Lys
65                  70                  75                  80

Val Ile Gly Arg Gly Ala Phe Gly Glu Val Gln Leu Val Arg His Lys
                85                  90                  95

Ser Thr Arg Lys Val Tyr Ala Met Lys Leu Leu Ser Lys Phe Glu Met
            100                 105                 110

Ile Lys Arg Ser Asp Ser Ala Phe Phe Trp Glu Glu Arg Asp Ile Met
        115                 120                 125
```

```
Ala Phe Ala Asn Ser Pro Trp Val Val Gln Leu Phe Tyr Ala Phe Gln
130                 135                 140

Asp Asp Arg Tyr Leu Tyr Met Val Met Glu Tyr Met Pro Gly Gly Asp
145                 150                 155                 160

Leu Val Asn Leu Met Ser Asn Tyr Asp Val Pro Glu Lys Trp Ala Arg
            165                 170                 175

Phe Tyr Thr Ala Glu Val Val Leu Ala Leu Asp Ala Ile His Ser Met
            180                 185                 190

Gly Phe Ile His Arg Asp Val Lys Pro Asp Asn Met Leu Leu Asp Lys
            195                 200                 205

Ser Gly His Leu Lys Leu Ala Asp Phe Gly Thr Cys Met Lys Met Asn
210                 215                 220

Lys Glu Gly Met Val Arg Cys Asp Thr Ala Val Gly Thr Pro Asp Tyr
225                 230                 235                 240

Ile Ser Pro Glu Val Leu Lys Ser Gln Gly Gly Asp Gly Tyr Tyr Gly
                245                 250                 255

Arg Glu Cys Asp Trp Trp Ser Val Gly Val Phe Leu Tyr Glu Met Leu
            260                 265                 270

Val Gly Asp Thr Pro Phe Tyr Ala Asp Ser Leu Val Gly Thr Tyr Ser
        275                 280                 285

Lys Ile Met Asn His Lys Asn Ser Leu Thr Phe Pro Asp Asp Asn Asp
290                 295                 300

Ile Ser Lys Glu Ala Lys Asn Leu Ile Cys Ala Phe Leu Thr Asp Arg
305                 310                 315                 320

Glu Val Arg Leu Gly Arg Asn Gly Val Glu Glu Ile Lys Arg His Leu
                325                 330                 335

Phe Phe Lys Asn Asp Gln Trp Ala Trp Glu Thr Leu Arg Asp Thr Val
            340                 345                 350

Ala Pro Val Val Pro Asp Leu Ser Ser Asp Ile Asp Thr Ser Asn Phe
        355                 360                 365

Asp Asp Leu Glu Glu Asp Lys Gly Glu Glu Glu Thr Phe Pro Ile Pro
370                 375                 380

Lys Ala Phe Val Gly Asn Gln Leu Pro Phe Val Gly Phe Thr Tyr Tyr
385                 390                 395                 400

Ser Asn Arg Arg Tyr Leu Ser Ser Ala Asn Pro Asn Asp Asn Arg Thr
                405                 410                 415

Ser Ser Asn Ala Asp Lys Ser Leu Gln Glu Ser Leu Gln Lys Thr Ile
            420                 425                 430

Tyr Lys Leu Glu Glu Gln Leu His Asn Glu Met Gln Leu Lys Asp Glu
        435                 440                 445

Met Glu Gln Lys Cys Arg Thr Ser Asn Ile Lys Leu Asp Lys Ile Met
        450                 455                 460

Lys Glu Leu Asp Glu Glu Gly Asn Gln Arg Arg Asn Leu Glu Ser Thr
465                 470                 475                 480

Val Ser Gln Ile Glu Lys Glu Lys Met Leu Leu Gln His Arg Ile Asn
            485                 490                 495

Glu Tyr Gln Arg Lys Ala Glu Gln Glu Asn Glu Lys Arg Arg Asn Val
        500                 505                 510

Glu Asn Glu Val Ser Thr Leu Lys Asp Gln Leu Glu Asp Leu Lys Lys
        515                 520                 525

Val Ser Gln Asn Ser Gln Leu Ala Asn Glu Lys Leu Ser Gln Leu Gln
530                 535                 540
```

-continued

```
Lys Gln Leu Glu Glu Ala Asn Asp Leu Leu Arg Thr Glu Ser Asp Thr
545                 550                 555                 560

Ala Val Arg Leu Arg Lys Ser His Thr Glu Met Ser Lys Ser Ile Ser
                565                 570                 575

Gln Leu Glu Ser Leu Asn Arg Glu Leu Gln Glu Arg Asn Arg Ile Leu
            580                 585                 590

Glu Asn Ser Lys Ser Gln Thr Asp Lys Asp Tyr Tyr Gln Leu Gln Ala
        595                 600                 605

Ile Leu Glu Ala Glu Arg Arg Asp Arg Gly His Asp Ser Glu Met Ile
    610                 615                 620

Gly Asp Leu Gln Ala Arg Ile Thr Ser Leu Gln Glu Glu Val Lys His
625                 630                 635                 640

Leu Lys His Asn Leu Glu Lys Val Glu Gly Glu Arg Lys Glu Ala Gln
                645                 650                 655

Asp Met Leu Asn His Ser Glu Lys Glu Lys Asn Asn Leu Glu Ile Asp
            660                 665                 670

Leu Asn Tyr Lys Leu Lys Ser Leu Gln Gln Arg Leu Glu Gln Glu Val
        675                 680                 685

Asn Glu His Lys Val Thr Lys Ala Arg Leu Thr Asp Lys His Gln Ser
    690                 695                 700

Ile Glu Ala Lys Ser Val Ala Met Cys Glu Met Glu Lys Lys Leu
705                 710                 715                 720

Lys Glu Glu Arg Glu Ala Arg Glu Lys Ala Glu Asn Arg Val Val Gln
                725                 730                 735

Ile Glu Lys Gln Cys Ser Met Leu Asp Val Asp Leu Lys Gln Ser Gln
            740                 745                 750

Gln Lys Leu Glu His Leu Thr Gly Asn Lys Glu Arg Met Glu Asp Glu
        755                 760                 765

Val Lys Asn Leu Thr Leu Gln Leu Glu Gln Glu Ser Asn Lys Arg Leu
    770                 775                 780

Leu Leu Gln Asn Glu Leu Lys Thr Gln Ala Phe Glu Ala Asp Asn Leu
785                 790                 795                 800

Lys Gly Leu Glu Lys Gln Met Lys Gln Glu Ile Asn Thr Leu Leu Glu
                805                 810                 815

Ala Lys Arg Leu Leu Glu Phe Glu Leu Ala Gln Leu Thr Lys Gln Tyr
            820                 825                 830

Arg Gly Asn Glu Gly Gln Met Arg Glu Leu Gln Asp Gln Leu Glu Ala
        835                 840                 845

Glu Gln Tyr Phe Ser Thr Leu Tyr Lys Thr Gln Val Lys Glu Leu Lys
    850                 855                 860

Glu Glu Ile Glu Glu Lys Asn Arg Glu Asn Leu Lys Lys Ile Gln Glu
865                 870                 875                 880

Leu Gln Asn Glu Lys Glu Thr Leu Ala Thr Gln Leu Asp Leu Ala Glu
                885                 890                 895

Thr Lys Ala Glu Ser Glu Gln Leu Ala Arg Gly Leu Leu Glu Glu Gln
            900                 905                 910

Tyr Phe Glu Leu Thr Gln Glu Ser Lys Lys Ala Ala Ser Arg Asn Arg
        915                 920                 925

Gln Glu Ile Thr Asp Lys Asp His Thr Val Ser Arg Leu Glu Glu Ala
    930                 935                 940

Asn Ser Met Leu Thr Lys Asp Ile Glu Ile Leu Arg Arg Glu Asn Glu
945                 950                 955                 960

Glu Leu Thr Glu Lys Met Lys Lys Ala Glu Glu Glu Tyr Lys Leu Glu
```

```
                   965                 970                 975
Lys Glu Glu Glu Ile Ser Asn Leu Lys Ala Ala Phe Glu Lys Asn Ile
                980                 985                 990
Asn Thr Glu Arg Thr Leu Lys Thr Gln Ala Val Asn Lys Leu Ala Glu
            995                1000                1005
Ile Met Asn Arg Lys Asp Phe Lys Ile Asp Arg Lys Lys Ala Asn Thr
       1010                1015                1020
Gln Asp Leu Arg Lys Lys Glu Lys Glu Asn Arg Lys Leu Gln Leu Glu
   1025                1030                1035                1040
Leu Asn Gln Glu Arg Glu Lys Phe Asn Gln Met Val Val Lys His Gln
               1045                1050                1055
Lys Glu Leu Asn Asp Met Gln Ala Gln Leu Val Glu Glu Cys Ala His
           1060                1065                1070
Arg Asn Glu Leu Gln Met Gln Leu Ala Ser Lys Glu Ser Asp Ile Glu
       1075                1080                1085
Gln Leu Arg Ala Lys Leu Leu Asp Leu Ser Asp Ser Thr Ser Val Ala
   1090                1095                1100
Ser Phe Pro Ser Ala Asp Glu Thr Asp Gly Asn Leu Pro Glu Ser Arg
1105                1110                1115                1120
Ile Glu Gly Trp Leu Ser Val Pro Asn Arg Gly Asn Ile Lys Arg Tyr
               1125                1130                1135
Gly Trp Lys Lys Gln Tyr Val Val Ser Ser Lys Lys Ile Leu Phe
           1140                1145                1150
Tyr Asn Asp Glu Gln Asp Lys Glu Gln Ser Asn Pro Ser Met Val Leu
       1155                1160                1165
Asp Ile Asp Lys Leu Phe His Val Arg Pro Val Thr Gln Gly Asp Val
   1170                1175                1180
Tyr Arg Ala Glu Thr Glu Glu Ile Pro Lys Ile Phe Gln Ile Leu Tyr
1185                1190                1195                1200
Ala Asn Glu Gly Glu Cys Arg Lys Asp Val Ala Leu Glu Ser Leu Gln
               1205                1210                1215
Thr Gln Lys Phe Thr Thr Lys Ser Asp Val Trp Ser Phe Gly Val Val
           1220                1225                1230
Leu Trp Glu Leu Met Thr Arg Gly Ala Pro Pro Tyr Pro Asp Val Asn
       1235                1240                1245
Thr Phe His Val Phe Lys Pro Pro Ala Leu Glu Cys Arg Arg Cys
   1250                1255                1260
His Val Lys Cys His Arg Asp His Leu Asp Lys Lys Glu Asp Leu Ile
1265                1270                1275                1280
Cys Pro Cys Lys Val Ser Tyr Asp Val Thr Ser Ala Arg Asp Met Leu
               1285                1290                1295
Leu Leu Ala Cys Ser Gln Asp Glu Gln Lys Lys Trp Val Thr His Leu
           1300                1305                1310
Val Lys Lys Ile Pro Lys Asn Pro Pro Ser Gly Phe Val Arg Ala Ser
       1315                1320                1325
Pro Arg Thr Leu Ser Thr Arg Ser Thr Ala Asn Gln Ser Phe Arg Lys
   1330                1335                1340
Val Val Lys Asn Thr Ser Gly Lys Thr Ser
1345                1350

<210> SEQ ID NO 2
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 2

Arg Arg Asn Ala
  1

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Lys Arg Asn Arg Thr Leu Ser Val
  1               5

<210> SEQ ID NO 4
<211> LENGTH: 400
<212> TYPE: PRT
<213> ORGANISM: Homo sapiens

<400> SEQUENCE: 4
```

Ala Phe Glu Thr Arg Phe Glu Lys Met Asp Asn Leu Leu Arg Asp Pro
  1               5                  10                  15

Lys Ser Glu Val Asn Ser Asp Cys Leu Leu Asp Gly Leu Asp Ala Leu
                 20                  25                  30

Val Tyr Asp Leu Asp Phe Pro Ala Leu Arg Lys Asn Lys Asn Ile Asp
             35                  40                  45

Asn Phe Leu Ser Arg Tyr Lys Asp Thr Ile Asn Lys Ile Arg Asp Leu
     50                  55                  60

Arg Met Lys Ala Glu Asp Tyr Glu Val Val Lys Val Ile Gly Arg Gly
 65                  70                  75                  80

Ala Phe Gly Glu Val Gln Leu Val Arg His Lys Ser Thr Arg Lys Val
                 85                  90                  95

Tyr Ala Met Lys Leu Leu Ser Lys Phe Glu Met Ile Ala Arg Ser Asp
            100                 105                 110

Ser Ala Phe Phe Trp Glu Glu Arg Asp Ile Met Ala Phe Ala Asn Ser
        115                 120                 125

Pro Trp Val Val Gln Leu Phe Tyr Ala Phe Gln Asp Asp Arg Tyr Leu
    130                 135                 140

Tyr Met Val Met Glu Tyr Met Pro Gly Gly Asp Leu Val Asn Leu Met
145                 150                 155                 160

Ser Asn Tyr Asp Val Pro Glu Lys Trp Ala Arg Phe Tyr Thr Ala Glu
                165                 170                 175

Val Val Leu Ala Leu Asp Ala Ile His Ser Met Gly Phe Ile His Arg
            180                 185                 190

Asp Val Lys Pro Asp Asn Met Leu Leu Asp Lys Ser Gly His Leu Lys
        195                 200                 205

Leu Ala Asp Phe Gly Thr Cys Met Lys Met Asn Lys Glu Gly Met Val
    210                 215                 220

Arg Cys Asp Thr Ala Val Gly Thr Pro Asp Tyr Ile Ser Pro Glu Val
225                 230                 235                 240

Leu Lys Ser Gln Gly Gly Asp Gly Tyr Tyr Gly Arg Glu Cys Asp Trp
                245                 250                 255

```
Trp Ser Val Gly Val Phe Leu Tyr Glu Met Leu Val Gly Asp Thr Pro
            260                 265                 270

Phe Tyr Ala Asp Ser Leu Val Gly Thr Ala Ser Lys Ile Met Asn His
        275                 280                 285

Lys Asn Ser Leu Thr Phe Pro Asp Asn Asp Ile Ser Lys Glu Ala
    290                 295                 300

Lys Asn Leu Ile Cys Ala Phe Leu Thr Asp Arg Glu Val Arg Leu Gly
305                 310                 315                 320

Arg Asn Gly Val Glu Glu Ile Lys Arg His Leu Phe Phe Lys Asn Asp
                325                 330                 335

Gln Trp Ala Trp Glu Thr Leu Arg Asp Thr Val Ala Pro Val Val Pro
                340                 345                 350

Asp Leu Ser Ser Asp Ile Asp Thr Ser Asn Phe Asp Asp Leu Glu Glu
            355                 360                 365

Ala Lys Gly Glu Glu Glu Thr Phe Pro Ile Pro Lys Ala Phe Val Gly
        370                 375                 380

Asn Gln Leu Pro Phe Val Gly Phe Thr Tyr Tyr Ser Asn Arg Arg Tyr
385                 390                 395                 400

<210> SEQ ID NO 5
<211> LENGTH: 398
<212> TYPE: PRT
<213> ORGANISM: Homo sapiens

<400> SEQUENCE: 5

Ala Ser Phe Glu Thr Arg Phe Glu Lys Met Asp Asn Leu Leu Arg Asp
1               5                   10                  15

Pro Lys Ser Glu Val Asn Ser Asp Cys Leu Leu Asp Gly Leu Asp Ala
            20                  25                  30

Leu Val Tyr Asp Leu Asp Phe Pro Ala Leu Arg Lys Asn Lys Asn Ile
        35                  40                  45

Asp Asn Phe Leu Ser Arg Tyr Lys Asp Thr Ile Asn Lys Ile Arg Asp
    50                  55                  60

Leu Arg Met Lys Ala Glu Asp Tyr Glu Val Val Lys Val Ile Gly Arg
65                  70                  75                  80

Gly Ala Phe Gly Glu Val Gln Leu Val Arg His Lys Ser Thr Arg Lys
                85                  90                  95

Val Tyr Ala Met Lys Leu Leu Ser Lys Phe Glu Met Ile Lys Arg Ser
            100                 105                 110

Asp Ser Ala Phe Phe Trp Glu Glu Arg Asp Ile Met Ala Phe Ala Asn
        115                 120                 125

Ser Pro Trp Val Val Gln Leu Phe Tyr Ala Phe Gln Asp Asp Arg Tyr
    130                 135                 140

Leu Tyr Met Val Met Glu Tyr Met Pro Gly Gly Asp Leu Val Asn Leu
145                 150                 155                 160

Met Ser Asn Tyr Asp Val Pro Glu Lys Trp Ala Arg Phe Tyr Thr Ala
                165                 170                 175

Glu Val Val Leu Ala Leu Asp Ala Ile His Ser Met Gly Phe Ile His
            180                 185                 190

Arg Asp Val Lys Pro Asp Asn Met Leu Leu Asp Lys Ser Gly His Leu
        195                 200                 205

Lys Leu Ala Asp Phe Gly Thr Cys Met Lys Met Asn Lys Glu Gly Met
    210                 215                 220

Val Arg Cys Asp Thr Ala Val Gly Thr Pro Asp Tyr Ile Ser Pro Glu
225                 230                 235                 240
```

―continued

```
Val Leu Lys Ser Gln Gly Gly Asp Gly Tyr Tyr Gly Arg Glu Cys Asp
            245             250             255

Trp Trp Ser Val Gly Val Phe Leu Tyr Glu Met Leu Val Gly Asp Thr
            260             265             270

Pro Phe Tyr Ala Asp Ser Leu Val Gly Thr Tyr Ser Lys Ile Met Asn
            275             280             285

His Lys Asn Ser Leu Thr Phe Pro Asp Ala Asn Asp Ile Ser Lys Glu
            290             295             300

Ala Lys Asn Leu Ile Cys Ala Phe Leu Thr Asp Arg Glu Val Arg Leu
305             310             315             320

Gly Arg Asn Gly Val Glu Glu Ile Lys Arg His Leu Phe Phe Lys Asn
            325             330             335

Asp Gln Trp Ala Trp Glu Thr Leu Arg Asp Thr Val Ala Pro Val Val
            340             345             350

Pro Asp Leu Ser Ser Asp Ile Asp Thr Ser Asn Phe Asp Asp Leu Glu
            355             360             365

Glu Asp Ala Gly Glu Glu Thr Phe Pro Ile Pro Lys Ala Phe Val
    370             375             380

Gly Asn Gln Leu Pro Phe Val Gly Phe Thr Tyr Tyr Ser Asn
385             390             395
```

CRYSTAL STRUCTURE OF RHO-KINASE I KINASE DOMAIN COMPLEXES AND BINDING POCKETS THEREOF

This application claims the benefit under 35 U.S.C. §119 of U.S. Provisional Application No. 60/695,161, filed Jun. 28, 2005, titled "CRYSTAL STRUCTURE OF RHO-KINASE I KINASE DOMAIN COMPLEXES AND BINDING POCKETS THEREOF".

This application refers to a "Sequence Listing", which is provided as an electronic document on two identical compact discs (CD-R), labeled "Copy 1" and "Copy 2." These compact discs each contain the electronic document, filename "VPI03-02 Sequence Listing.txt" (19,289 bytes in size, created on Jan. 30, 2007), which is hereby incorporated in its entirety herein.

TECHNICAL FIELD OF INVENTION

The present invention relates to Rho-kinase I (ROCK I) and ROCK I-like binding pockets, and computers comprising a data storage medium encoded with the structure coordinates of such binding pockets. This invention also relates to methods of using ROCK I structure coordinates to solve the structure of homologous proteins or protein complexes. In addition, this invention relates to methods of using ROCK I structure coordinates for screening, identifying, and designing compounds, including inhibitory compounds, that bind to ROCK I protein, ROCK I protein homologues, or complexes thereof. The invention also relates to crystallizable compositions and crystals comprising ROCK I kinase domain and ROCK I kinase domain complexed with an inhibitor of that domain.

BACKGROUND OF THE INVENTION

RhoA is a small GTPase in the Ras homology family exhibiting both GDP/GTP binding and GTPase activities. Like other GTPase molecules, RhoA cycles from an active or GTP-bound conformation to an inactive or GDP-bound conformation by hydrolysis of GTP to GDP. The activation of RhoA plays a key role in $Ca^{+2}$-independent smooth muscle contraction.

Two isoforms of Rho-kinase, known as Rho-kinase α and β or ROCK II and I, respectively, are important downstream targets of activated RhoA. The α and β isoforms have 64% sequence identity overall and kinase domains that are 90% identical. ROCK I is composed of an N-terminal catalytic kinase domain, a coiled-coil domain, and a C-terminal pleckstrin homology (PH) domain. These domains are common to other closely related kinases, including myotonic dystrophy kinase (DMPK), myotonic dystrophy kinase-related Cdc42-binding kinase (MRCK), and citron kinase, except that an additional short coiled-coil domain segment N-terminal to the catalytic domain has been identified in ROCK I (amino acid residues 47-78) and in ROCK II (amino acid residues 63-93) (Amano et al., *J. Biol. Chem.* 274:32418-32424 (1999)). This short coiled-coil segment is absent in DMPK and MRCK.

Rho-kinases regulate muscle myosin light chain (MLC) proteins both by direct phosphorylation (Kureishi et al., *J. Biol. Chem.* 272:12257-12260 (1997); Amano et al., *J. Biol. Chem.* 271:20246-20249 (1996)) and indirectly by phosphorylation of the myosin binding subunit of myosin phosphatase. This phosphorylation inhibits the phosphatase activity, leading to increased levels of phosphorylated MLCs, followed by subsequent muscle contraction (Totsukawa et al., *J. Cell. Biol.* 150:797-806 (2000)). The Rho/ROCK pathway is also involved in nonmuscle myosin regulation and has been implicated in stress fiber and focal adhesion formation (Ishizaki et al., *FEBS Lett.* 404:118-124 (1997)); Kawano et al., *J. Cell Biol.* 147:1023-1038 (1999)), neurite retraction (Amano et al., *Genes Cells* 3:177-188 (1998)); Hirose et al., *J. Cell Biol.* 141:1625-1636 (1998)), and tumor cell invasion (Yoshioka et al., *J. Biol. Chem.* 273:5146-5154 (1998)); Sahai and Marshall, *Nat. Cell. Biol.* 5, 711-719 (2003)) in non-muscle cells. Overexpression of RhoA has been associated with colon, breast, lung, and testicular germ cell cancers and in head and neck squamous-cell carcinomas (Sahai, et al., *Nature Reviews Cancer* 2:133-142 (2002)).

Given the importance of ROCK in regulating such key regulatory processes, structural information on the unique features of the active site of ROCK I would facilitate the discovery of drugs for diseases or disorders in which ROCK plays a role.

SUMMARY OF THE INVENTION

The present invention provides crystal structures of ROCK I-inhibitor complexes. In one aspect, the invention provides molecules or molecular complexes comprising ROCK I binding pockets, or ROCK I-like binding pockets that have similar three-dimensional shapes. In one embodiment, the molecules are ROCK I kinase domains or homologues thereof. In another embodiment, the molecular complexes are ROCK I kinase domain complexes or homologues thereof. In another embodiment, the molecules or molecular complexes are in crystalline form.

The invention also provides crystallizable compositions and crystals comprising ROCK I kinase domain, complexes thereof, or homologues thereof.

In another aspect, the invention provides a computer comprising a machine-readable storage medium that includes data defining a ROCK I or ROCK I-like binding pocket or domain according to the structure coordinates of Table 2, 3, 4, or 5. Such a storage medium, when read and utilized by a computer programmed with appropriate software, can display a three-dimensional graphical representation of such binding pockets or domains on a computer monitor or similar viewing device. In one embodiment, the structure coordinates of said binding pocket or domain are produced by homology modeling of at least a portion of the structure coordinates of Table 2, 3, 4, or 5.

The invention also further provides methods for designing, selecting, evaluating, identifying, and/or optimizing compounds that bind to the ROCK I molecules or molecular complexes or their binding pockets. In one embodiment, such compounds are inhibitors of ROCK I, ROCK I-like proteins or homologues thereof.

The invention also provides methods for determining at least a portion of the three-dimensional structure of molecules or molecular complexes which contain at least some structurally similar features to ROCK I, particularly ROCK I homologues. Such methods are achieved by using at least some of the structure coordinates obtained from the ROCK I catalytic domain.

DETAILED DESCRIPTION OF THE INVENTION

Figure 1:
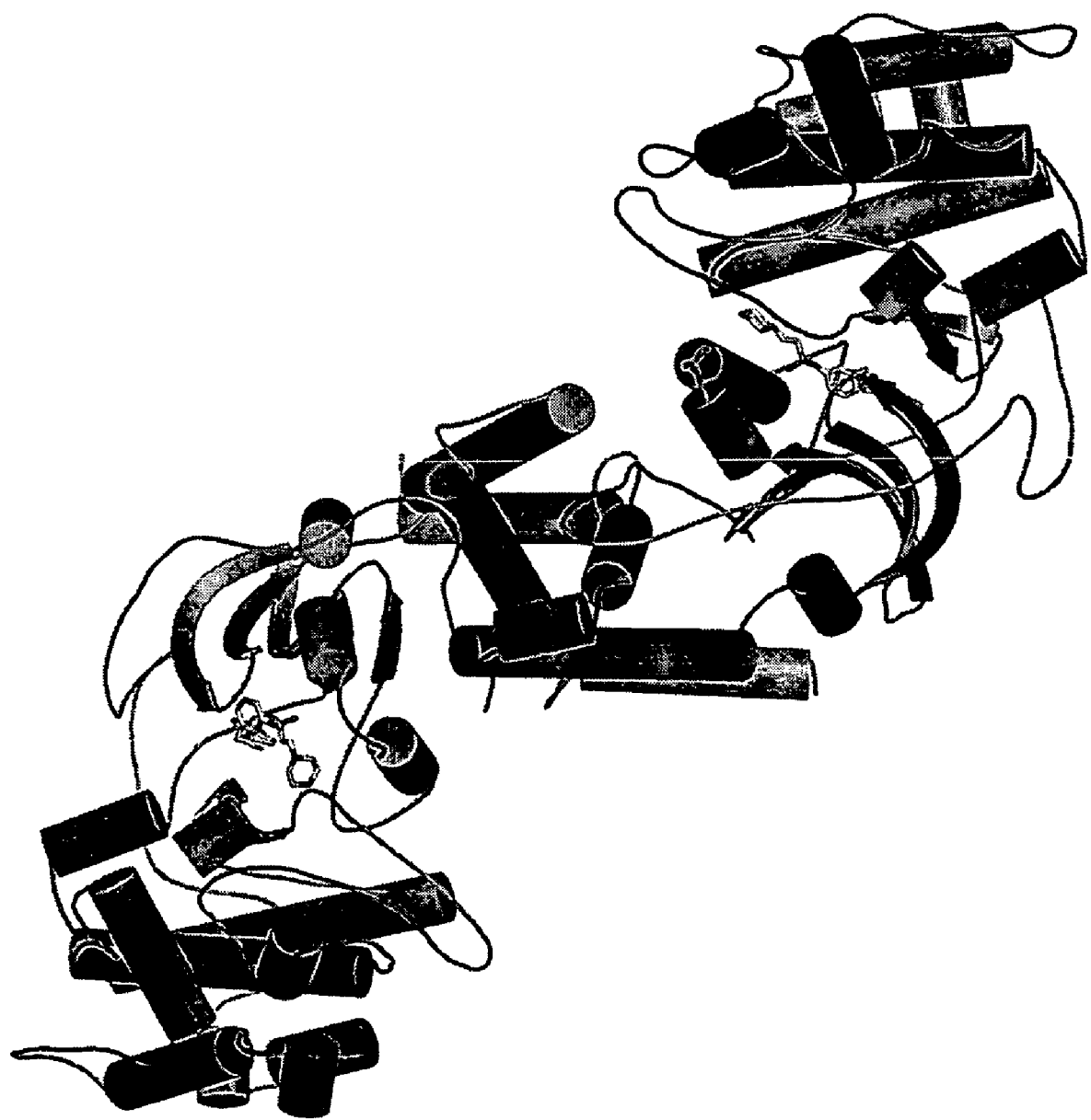
FIG. 1 depicts a diagram of the overall fold of a ROCK I-inhibitor complex.

In order that the invention described herein may be more fully understood, the following detailed description is set forth.

Throughout the specification, the word "comprise", or variations such as "comprises" or "comprising" will be understood to imply the inclusion of a stated integer or groups of integers but not exclusion of any other integer or groups of integers.

The following abbreviations are used throughout the application:

| | | | | | |
|---|---|---|---|---|---|
| A = | Ala = | Alanine | T = | Thr = | Threonine |
| V = | Val = | Valine | C = | Cys = | Cysteine |
| L = | Leu = | Leucine | Y = | Tyr = | Tyrosine |
| I = | Ile = | Isoleucine | N = | Asn = | Asparagine |
| P = | Pro = | Proline | Q = | Gln = | Glutamine |
| F = | Phe = | Phenylalanine | D = | Asp = | Aspartic Acid |
| W = | Trp = | Tryptophan | E = | Glu = | Glutamic Acid |
| M = | Met = | Methionine | K = | Lys = | Lysine |
| G = | Gly = | Glycine | R = | Arg = | Arginine |
| S = | Ser = | Serine | H = | His = | Histidine |

As used herein, the following definitions shall apply unless otherwise indicated.

The term "about" when used in the context of root mean square deviation (RMSD) values takes into consideration the standard error of the RMSD value, which is ±0.1 Å.

The term "associating with" refers to a condition of proximity between a chemical entity or compound, or portions thereof, and a binding pocket or binding site on a protein. The association may be non-covalent—wherein the juxtaposition is energetically favored by hydrogen bonding, hydrophobic, van der Waals or electrostatic interactions—or it may be covalent. The association or interaction of a chemical entity with a binding pocket or domain may be measured by interaction energy, free energy of binding or deformation energy of the chemical entity.

The term "ATP analogue" refers to a compound derived from adenosine-5'-triphosphate (ATP). The compound can be adenosine, AMP, ADP, or a non-hydrolyzable analogue, such as, but not limited to an inhibitor. The analogue may be in complex with magnesium or manganese ions.

The term "binding pocket" refers to a region of a molecule or molecular complex, that, as a result of its shape, favorably associates with another chemical entity. The term "pocket" includes, but is not limited to, a cleft, channel or site. ROCK I, ROCK I-like molecules, or homologues thereof, may have binding pockets which include, but are not limited to, peptide or substrate binding sites, inhibitor-binding pocket and ATP-binding sites. The shape of a binding pocket may be largely pre-formed before binding of a chemical entity, may be formed simultaneously with binding of a chemical entity thereto, or may be formed by the binding of another chemical entity thereto to a different binding pocket of the molecule, which in turn induces a change in shape of the binding pocket.

The term "catalytic active site" or "active site" refers to the portion of the protein kinase to which a nucleotide substrate binds. For example, the catalytic active site of ROCK I is at the interface between the N-terminal and C-terminal domains thereof.

The term "catalytic domain", "kinase catalytic domain", "protein kinase catalytic domain" or "catalytic kinase domain" refers to the kinase domain of a kinase protein. The kinase domain includes the catalytic active site.

The term "chemical entity" refers to chemical compounds, complexes of at least two chemical compounds, and fragments of such compounds or complexes. The chemical entity can be, for example, a ligand, substrate, nucleotide triphosphate, nucleotide diphosphate, nucleotide monophosphate, nucleotide, agonist, antagonist, inhibitor, antibody, peptide, protein or drug. In one embodiment, the chemical entity is an inhibitor or substrate for the active site of a ROCK I protein or protein complex, or homologues thereof. The "first" and "second" chemical entities referred to in the present invention may be identical or distinct from each other.

The term "conservative substitutions" refers to residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., *Atlas of Protein Sequence and Structure*, 5: 345-352 (1978 & Supp.), which is incorporated herein by reference. Examples of conservative substitutions are substitutions including but not limited to the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine; and (h) phenylalanine, tyrosine.

The term "contact score" refers to a measure of shape complementarity between a chemical entity and binding pocket, which is correlated with an RMSD value obtained from a least square superimposition between all or part of the atoms of the chemical entity and all or part of the atoms of the ligand bound (for example, inhibitor) in the binding pocket according to Table 2, 3, 4, or 5. The docking process may be facilitated by the contact score or RMSD values. For example, if the chemical entity moves to an orientation with high RMSD, the system will resist the motion. A set of orientations of a chemical entity can be ranked by contact score. A lower RMSD value will give a higher contact score. See Meng et al. *J. Comp. Chem.* 4: 505-524 (1992).

The term "correspond to" or "corresponding amino acid," when used in the context of amino acid residues, that correspond to human ROCK I amino acid residues, refers to particular amino acid residues or analogues thereof in a ROCK I homologue that correspond to amino acid residues in the human ROCK I protein. The corresponding amino acid may be an identical, mutated, chemically modified, conserved, conservatively substituted, functionally equivalent or homologous amino acid residue, when compared to the human ROCK I amino acid residue to which it corresponds.

Methods for identifying a corresponding amino acid are known in the art and are based upon sequence, structural alignment, its functional position, or a combination thereof, as compared to a ROCK I kinase. For example, corresponding amino acids may be identified by superimposing the backbone atoms of the amino acids in ROCK I and the protein using well known software applications, such as QUANTA (Accelrys, San Diego, Calif. ©2001, 2002). The corresponding amino acids may also be identified using sequence alignment programs such as the "bestfit" program or CLUSTAL W Alignment Tool (Higgins et al., *Methods Enzymol.* 266: 383-402 (1996)).

The term "crystallization solution" refers to a solution that promotes crystallization comprising at least one agent, including a buffer, one or more salts, a precipitating agent, one or more detergents, sugars or organic compounds, lanthanide ions, a poly-ionic compound and/or a stabilizer.

The term "docking" refers to orienting, rotating, translating a chemical entity in the binding pocket, domain, molecule or molecular complex or portion thereof based on distance geometry or energy. Docking may be performed by distance geometry methods that find sets of atoms of a chemical entity that match sets of sphere centers of the binding pocket, domain, molecule or molecular complex or portion thereof. See Meng et al. *J. Comp. Chem.* 4: 505-524 (1992). Sphere centers are generated by providing an extra radius of given length from the atoms (excluding hydrogen atoms) in the binding pocket, domain, molecule or molecular complex or portion thereof. Real-time interaction energy calculations, energy minimizations or rigid-body minimizations (Gschwend et al., *J. Mol. Recognition* 9:175-186 (1996)) can be performed while orienting the chemical entity to facilitate docking. For example, interactive docking experiments can be designed to follow the path of least resistance. If the user in an interactive docking experiment makes a move to increase the energy, the system will resist that move. However, if that user makes a move to decrease energy, the system will favor that move by increased responsiveness. (Cohen et al., *J. Med. Chem.* 33:889-894 (1990)). Docking can also be performed by combining a Monte Carlo search technique with rapid energy evaluation using molecular affinity potentials. See Goodsell and Olson, *Proteins: Structure, Function and Genetics* 8:195-202 (1990). Software programs that carry out docking functions include, but are not limited to, MATCH-MOL (Cory et al., *J. Mol. Graphics* 2: 39 (1984); MOLFIT (Redington, *Comput. Chem.* 16 217 (1992)) and DOCK (Meng et al., supra).

The term "domain" refers to a structural unit of a ROCK I protein or homologue. The domain can comprise a binding pocket, a sequence or a structural motif.

The term "full-length ROCK I" or "human ROCK I protein" refers to the complete human ROCK I protein (amino acid residues 1 to 1390; GenBank Accession No. P08581; SEQ ID NO:1).

The term "generating a three-dimensional structure" or "generating a three-dimensional representation" refers to converting the lists of structure coordinates into structural models or graphical representation in three-dimensional space. This can be achieved through commercially or publicly available software. A model of a three-dimensional structure of a molecule or molecular complex can thus be constructed on a computer screen by a computer that is given the structure coordinates and that comprises the correct software. The three-dimensional structure may be displayed or used to perform computer modeling or fitting operations. In addition, the structure coordinates themselves, without the displayed model, may be used to perform computer-based modeling and fitting operations.

The term "homologue of ROCK I kinase domain" or "ROCK I kinase domain homologue" refers to a protein kinase or protein kinase domain that is at least 80% identical in sequence to the human ROCK I kinase domain and retains Rho-kinase activity. In other embodiments of this invention, the homologue is at least 80%, 85%, 90%, 95%, 96%, 97%, 98% or 99% identical in sequence to human ROCK I kinase domain, and has conservative mutations, as compared to human ROCK I kinase domain. The homologue can be ROCK I kinase domain from another species, or human ROCK I kinase domain with conservative substitutions. Such animal species include, but are not limited to, mouse, rat, a primate such as monkey or other primates.

The term "homologue of ROCK I protein" or "ROCK I protein homologue" refers to a protein that is at least 80% identical in sequence to the full-length human ROCK I protein and retains Rho-kinase activity. In other embodiments of this invention, the homologue is at least 80%, 85%, 90%, 95%, 96%, 97%, 98% or 99% identical in sequence to human ROCK I protein and has conservative mutations, as compared to human ROCK I protein. The homologue can be ROCK I protein from another species, or human ROCK I protein with conservative substitutions. Such animal species include, but are not limited to, mouse, rat, a primate such as monkey or other primates.

The term "homology model" refers to a structural model derived from known three-dimensional structure(s). Generation of the homology model, termed "homology modeling", can include sequence alignment, residue replacement, residue conformation adjustment through energy minimization, or a combination thereof.

The term "interaction energy" refers to the energy determined for the interaction of a chemical entity and a binding pocket, domain, molecule or molecular complex or portion thereof. Interactions include, but are not limited to, one or more of covalent interactions, non-covalent interactions such as hydrogen bond, electrostatic, hydrophobic, aromatic, van der Waals interactions, and non-complementary electrostatic interactions such as repulsive charge-charge, dipole-dipole and charge-dipole interactions. As interaction energies are measured in negative values, the lower the value indicates the more favorable the interaction.

The term "ROCK I ATP-binding pocket" refers to a binding pocket of a molecule or molecular complex defined by the structure coordinates of a certain set of amino acid residues present in the ROCK I structure, as described below. In general, the ligand for the ATP-binding pocket is a nucleotide such as ATP. This binding pocket is in the catalytic active site of the catalytic domain. In the protein kinase family, the ATP-binding pocket is generally located at the interface of the N-terminal and C-terminal domains, and is bordered by the glycine rich loop and the hinge (See Xie et al., *Structure* 6: 983-991 (1998), incorporated herein by reference).

The term "ROCK I inhibitor-binding pocket" refers to that portion of the ROCK I enzyme active site to which the inhibitor binds. The inhibitor-binding pocket is defined by the structure coordinates of a certain set of amino acid residues present in the ROCK I-inhibitor structure, as described below.

The term "ROCK I-like" refers to all or a portion of a molecule or molecular complex that has a commonality of shape with all or a portion of the ROCK I protein. For example, in the ROCK I-like inhibitor-binding pocket, the commonality of shape is defined by a root mean square deviation of the structure coordinates of the backbone atoms between the amino acids in the ROCK I-like inhibitor-binding pocket and the ROCK I amino acids in the ROCK I inhibitor-binding pocket, as set forth in Table 2, 3, 4, or 5. Compared to the amino acids of the ROCK I inhibitor-binding pocket, the corresponding amino acid residues in the ROCK I-like inhibitor-binding pocket may or may not be identical. Depending on the set of ROCK I amino acid residues that define the ROCK I inhibitor-binding pocket, one skilled in the art would be able to locate the corresponding amino acid residues that define a ROCK I-like inhibitor-binding pocket in a protein, based on sequence or structural homology.

The term "ROCK I kinase domain complex" or "ROCK I kinase domain homologue complex" refers to a molecular complex formed by associating the ROCK I kinase domain or ROCK I kinase domain homologue with a chemical entity, for example, a ligand, a substrate, nucleotide triphosphate, nucleotide diphosphate, nucleotide monophosphate, an agonist or antagonist, inhibitor, antibody, drug, or compound.

The term "motif" refers to a group of amino acid residues in the ROCK I kinase or homologue that defines a structural compartment or carries out a function in the protein, for example, catalysis, structural stabilization or phosphorylation. The motif may be conserved in sequence, structure, and function. The motif can be contiguous in primary sequence or three-dimensional space. Examples of a motif include, but are not limited to, a binding pocket, activation loop, the glycine-rich loop, and the DFG loop (See Xie et al., *Structure* 6: 983-991 (1998)).

The term "part of a binding pocket" refers to less than all of the amino acid residues that define the binding pocket. The structure coordinates of amino acid residues that constitute part of a binding pocket may be specific for defining the chemical environment of the binding pocket, or useful in designing fragments of an inhibitor that may interact with those residues. For example, the portion of amino acid residues may be key residues that play a role in ligand binding, or may be residues that are spatially related and define a three-dimensional compartment of the binding pocket. The amino acid residues may be contiguous or non-contiguous in primary sequence. In one embodiment, part of the binding pocket has at least two amino acid residues, preferably at least three, six, eight, ten, fourteen, or fifteen amino acid residues.

The term "part of a ROCK I kinase domain" or "part of a ROCK I kinase domain homologue" refers to less than all of the amino acid residues of a ROCK I kinase domain or homologue. In one embodiment, part of the ROCK I kinase domain or homologue thereof defines the binding pockets, sub-domains, and motifs of the kinase domain or homologue. The structure coordinates of amino acid residues that constitute part of a ROCK I kinase domain or ROCK I kinase domain homologue may be specific for defining the chemical environment of the domain, or useful in designing fragments of an inhibitor that interact with those residues. The portion of amino acid residues may also be residues that are spatially related and define a three-dimensional compartment of the binding pocket, motif, or domain. The amino acid residues may be contiguous or non-contiguous in primary sequence. For example, the portion of amino acid residues may be key residues that play a role in ligand or substrate binding, peptide binding, antibody binding, catalysis, structural stabilization, or degradation.

The term "quantified association" refers to calculations of distance geometry and energy. Energy can include, but is not limited to, interaction energy, free energy and deformation energy. See Cohen, supra.

The term "human ROCK I kinase domain" refers to amino acids 1-415 of SEQ ID NO:1 with up to about 5 amino acid deletions at the N-terminal, and up to about 13 amino acid deletions at the C-terminal. In one embodiment, the ROCK I kinase domain is any of amino acid residues 6-415, 6-402, or 1-402 of SEQ ID NO:1.

The term "root mean square deviation" or "RMSD" means the square root of the arithmetic mean of the squares of the deviations from the mean. It is a way to express the deviation or variation from a trend or object. For purposes of the invention, the "root mean square deviation" defines the variation in the backbone atoms of ROCK I, a binding pocket, a motif, a domain, or portion thereof, as defined by the structure coordinates of ROCK I described herein. It would be apparent to the skilled worker that the calculation of RMSD involves a standard error of ±0.1 Å.

The term "soaked" refers to a process in which a crystal is transferred to a solution containing the compound of interest.

The term "structure coordinates" refers to Cartesian coordinates derived from mathematical equations related to the patterns obtained on diffraction of a monochromatic beam of X-rays by the atoms (scattering centers) of a protein or protein complex in crystal form. The diffraction data are used to calculate an electron density map of the repeating unit of the crystal. The electron density maps are then used to establish the positions of the individual atoms of the molecule or molecular complex.

The term "sub-domain" refers to a portion of the domain.

The term "substantially all of a ROCK I binding pocket" or "substantially all of a ROCK I kinase domain" refers to all or almost all of the amino acids in the ROCK I binding pocket or protein. For example, substantially all of a ROCK I binding pocket can be 100%, 95%, 90%, 80%, or 70% of the amino acid residues defining the ROCK I binding pocket or domain.

The term "substrate binding pocket" refers to the binding pocket for a substrate of ROCK I or a homologue thereof. A "substrate" is generally defined as the molecule upon which an enzyme performs catalysis. Natural substrates, synthetic substrates or peptides, or mimics of natural substrates of ROCK I or a homologue thereof may associate with the substrate binding pocket.

The term "sufficiently homologous to ROCK I kinase domain" refers to a protein that has a sequence identity of at least 25% compared to ROCK I kinase domain. In other embodiments of this invention, the sequence identity is at least 40%. In further embodiments, the sequence identity is at least 50%, 60%, 70%, 80%, 90%, 95%, 96%, 97%, 98%, or 99%.

The term "three-dimensional structural information" refers to information obtained from the structure coordinates. Structural information generated can include the three-dimensional structure or graphical representation of the structure. Structural information can also be generated when subtracting distances between atoms in the structure coordinates, calculating chemical energies for a ROCK I molecule, molecular complex, or homologue thereof, or calculating and/or minimizing energies for an association of a ROCK I molecule, molecular complex, or homologues thereof to a chemical entity.

Crystallizable Compositions and Crystals of ROCK I Kinase Domain and Complexes Thereof According to one aspect, the invention provides a crystal or crystallizable composition comprising a human ROCK I kinase domain, a human ROCK I kinase domain homologue, a human ROCK I kinase domain in complex with a chemical entity, or a human ROCK I kinase domain homologue in complex with a chemical entity. In one embodiment, the chemical entity is an ATP analogue, nucleotide triphosphate, nucleotide diphosphate, nucleotide monophosphate, adenosine, or an active site inhibitor. Non-limiting examples of chemical entities that can be included in the ROCK I complex are 3-phenyl-1-(4-(pyridin-4-yl)thiazol-2-yl)piperidin-2-one (inhibitor2), 2-(3-(3-(4-methylpiperazin-1-yl)propoxy)phenyl)-N-(4-(pyridin-4-yl)thiophen-2-yl)acetamide (inhibitor3), 2-(5-bromobenzo[d][1,3]dioxol-6-yl)-N-(4-(pyridin-4-yl)thiazol-2-yl)acetamide (inhibitor4) or N—((S)-2-hydroxy-1-phenylethyl)-4-(1H-pyrazolo[3,4-b]pyridin-3-yl)-1H-pyrrole-2-carboxamide (inhibitor5). Applicant has previously described these compounds in International Publication WO2004/041813 and WO2006/058120, the disclosures of which are incorporated herein by reference.

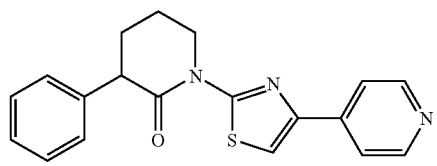

3-phenyl-1-(4-(pyridin-4-yl)thiazol-2-yl)piperidin-2-one (inhibitor2)

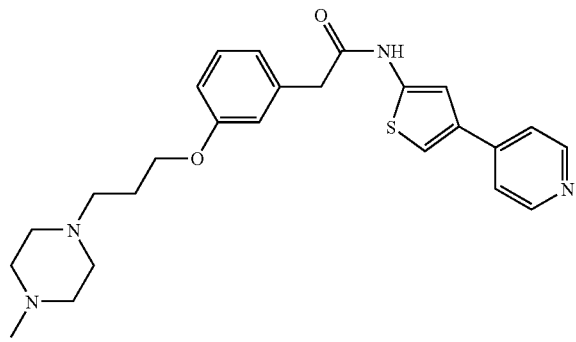

2-(3-(3-(4-methylpiperazin-1-yl)propoxy)phenyl)-N-(4-(pyridin-4-yl)thiophen-2-yl)acetamide (inhibitor3)

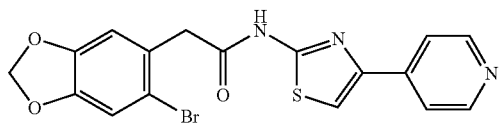

2-(5-bromobenzo[d][1,3]dioxol-6-yl)-N-(4-(pyridin-4-yl)thiazol-2-yl)acetamide (inhibitor4)

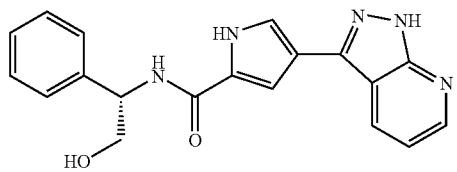

N—((S)-2-hydroxy-1-phenylethyl)-4-(1H-pyrazolo[3,4-b]pyridin-3-yl)-1H-pyrrole-2-carboxamide (inhibitor5)

According to another embodiment, the chemical entity is an active site inhibitor, wherein the active site inhibitor is a compound of Formula I:

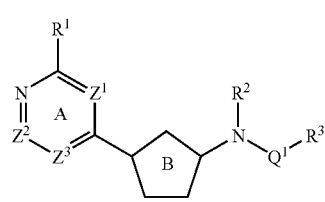

or a pharmaceutically acceptable salt thereof, wherein:

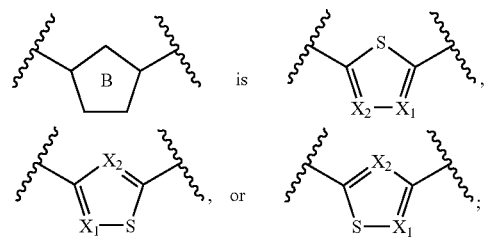

$R^1$ is halogen, CN, $NO_2$, or $V_mR$;

$Z^1$ and $Z^3$ are each independently N or $CR^Z$, and $Z^2$ is N or $CR^1$, provided that $Z^1$, $Z^2$ and $Z^3$ are not simultaneously N;

each occurrence of $R^Z$ is independently halogen, CN, $NO_2$, or $U_nR'$;

$R^2$ is $U_nR'$;

$X^1$ and $X^2$ are each independently $CR^4$ or N;

each occurrence of $R^4$ is independently halogen, CN, $NO_2$, or $V_mR$;

each occurrence of U or V is independently an optionally substituted $C_{1-6}$ alkylidene chain, wherein up to two methylene units of the chain are optionally and independently replaced by —NR—, —S—, —O—, —CS—, —$CO_2$—, —OCO—, —CO—, —COCO—, —CONR—, —NRCO—, —$NRCO_2$—, —$SO_2NR$—, —$NRSO_2$—, —CONRNR—, —NRCONR—, —OCONR—, —NRNR—, —$NRSO_2NR$—, —SO—, —$SO_2$—, —PO—, —$PO_2$—, or —POR—;

m and n are each independently 0 or 1;

each occurrence of R is independently hydrogen or an optionally substituted $C_{1-6}$ aliphatic group; and each occurrence of R' is independently hydrogen or an optionally substituted $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

$Q^1$ is —CO—, —$SO_2$—, —CONR—, or —$SO_2NR$—;

$R^3$ is $Q^2$-$Ar^1$, or $R^2$ and $Q^1$-$R^3$, taken together with the nitrogen atom, form the cyclic group:

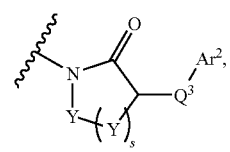

where s is 1 or 2, each occurrence of Y is independently, as valency and stability permit, —CO—, —CS—, —$SO_2$—, —O—, —S—, —$NR^5$—, or —$C(R^5)_2$—, and $R^5$ is $U_nR'$;

$Q^2$ and $Q^3$ are each independently a bond or a $C_{1-6}$ alkylidene chain, wherein up to two methylene units of the chain are each optionally and independently replaced by —NR'—, —S—, —O—, —CS—, —CO$_2$—, —OCO—, —CO—, —COCO—, —CONR'—, —NR'CO—, —NR'CO$_2$—, —SO$_2$NR'—, —NR'SO$_2$—, —CONR'NR'—, —NR'CONR'—, —OCONR'—, —NR'NR'—, —NR'SO$_2$NR'—, —SO—, —SO$_2$—, —PO—, —PO$_2$—, or —POR'—; and wherein any carbon atom in the one or more methylene units is optionally substituted with one or two occurrences of $R^6$, wherein each occurrence of $R^6$ is independently halogen, CN, NO$_2$, or U$_n$R', or two occurrences of $R^6$, or R' and $R^6$, taken together with the atoms to which they are bound, form an optionally substituted 3-6-membered cycloalkyl, heterocyclyl, aryl or heteroaryl ring; and $Ar^1$ and $Ar^2$ are each independently a 5-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $Ar^1$ and $Ar^2$ are each optionally substituted with 0-5 independent occurrences of $TR^7$; wherein T is a bond or is a $C_1$-$C_6$ alkylidene chain wherein up to two methylene units of T are optionally and independently replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, or —POR—; and each occurrence of $R^7$ is independently R', halogen, NO$_2$, or CN. Applicant has previously described examples of these compounds in International Publication WO2004/041813, the disclosure of which is incorporated herein by reference.

In one embodiment: I. for compounds described where

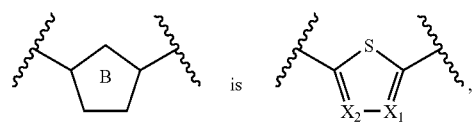

one or more of, or all of the following conditions apply:
A) for compounds having the structure:

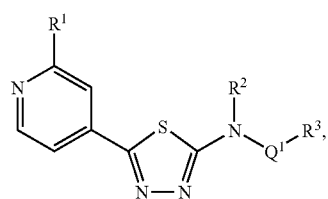

i) when $R^1$ is Cl, and $R^2$ is —CH(CH$_3$)COOCH$_3$ or hydrogen, then $Q^1$-$R^3$ is not —CO(unsubstituted phenyl), —CO(unsubstituted 2-furyl), or —COCH$_2$(unsubstituted phenyl);

ii) when $R^1$ is hydrogen, $R^2$ is hydrogen, and $Q^1$ is —CO—, then $R^3$ is not:
a) phenyl substituted with 4-O(CH$_2$)$_{4-7}$CH$_3$ or 4-(CH$_2$)$_{4-7}$CH$_3$;
b) phenyl substituted with 2-Cl, 4-NO$_2$, 4-Cl, 2-Br, 3-Br, 3-I, 3-CH$_3$, 4-OCH$_3$, 3-NO$_2$, or 4-I;
c) 2,6-OCH$_3$-phenyl
d) (5-Cl, 3-CH$_3$, 1-phenyl)-pyrazol-4-yl; or
e) 4-OnBu-phenyl, —CH$_2$O(2-F-phenyl), —(CH$_2$)$_2$phenyl, furan-2-yl, thiophen-2-yl, 4-CH$_3$-phenyl, —CH$_2$O(2-CH$_3$-phenyl), 3-OCH$_3$-phenyl, 2-(2,5-dimethoxylphenyl)quinolin-4-yl, —NH-(4-Cl-phenyl), —NH-(3,4-dichlorophenyl), (2-CO$_2$H, 3-NO$_2$)-phenyl, 3,5-dimethyl-ixoxazol-4-yl, —CH═CH-phenyl, 4-F-phenyl, C(CH$_3$)$_2$O-(4-Cl-phenyl), —NH(3-Cl-phenyl), —NHphenyl, unsubstituted phenyl, 3,4,5-OCH$_3$-phenyl, 4-NO$_2$-phenyl, 4-cyclopentoxy-phenyl, —(CH$_2$)$_3$phenyl, -(tricyclo[3.3.1.13,7]decan-1-yl, —CH$_2$O-(3-CH$_3$-phenyl), 3-NO$_2$-phenyl, -cyclopropyl-(4-tert-butyl-phenyl), 2,3-OCH$_3$-phenyl, 1,3-benzodioxo-5-yl, —CH$_2$—O-(4-F-phenyl), or 3-Br-phenyl;
iii) when $R^1$ is hydrogen, $R^2$ is hydrogen, and $Q^1$ is —CSNH—, then $R^3$ is not 2,3,4,6-tetra-O-acetyl-β-D-glucopyranosyl;
iv) when $R^1$ is hydrogen, $R^2$ is hydrogen, and $Q^1$ is SO$_2$, then $R^3$ is not unsubstituted phenyl, unsubstituted benzyl, unsubstituted naphthyl, phenyl substituted with para-NHCOCH$_3$, para-NH$_2$, or para-CH$_3$; and
v) when $R^1$ is hydrogen, $R^2$ is —CH$_2$CH═CH$_2$, and $Q^1$ is CO, then $R^3$ is not 4-OCH$_3$-phenyl, unsubstituted naphthyl, —NH-(4-OCH$_3$-phenyl), 3,5-OCH$_3$-phenyl, —CH$_2$Ophenyl, —CH$_2$-thiophen-2-yl, or —CH(phenyl)(CH$_2$CH$_3$); and
vi) when $R^1$ is hydrogen, $R^2$ is CH$_2$CH$_3$, and $Q^1$ is CO, then $R^3$ is not 2,4-Cl-phenyl; and
B) for compounds having the structure:

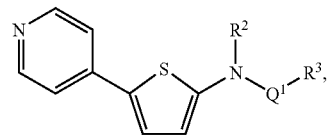

when $R^2$ is hydrogen or CH$^3$, and $Q^1$ is —CO—, then $R^3$ is not —OCH$_2$CH$_2$OCH$_2$phenyl;
II. for compounds described where

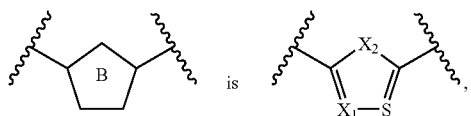

is one or more of, or all of the following conditions apply:
A) for compounds having the structure:

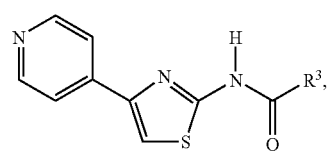

i) when $R^3$ is $Q^2$-$Ar^1$, and $Q^2$ is a bond then $Ar^1$ is not any one or more of the following: unsubstituted phenyl or phenyl substituted with 2-Br; 2-Cl; 2-I; 2,6-F; 3,5-OCH$_3$; 3,4,5-OCH$_3$; 2,4-OCH$_3$; 3,4-CH$_3$; 2,5-Cl; 3,4,—OCH$_3$; 2-Cl, 5-NO$_2$; 3,5-Cl; 3-O(CH$_2$)$_4$CH$_3$, 3-O-n-butyl, 3-CF$_3$, 3-OCH$_3$, 3-Br; 3-NO$_2$; 3-CH$_3$; 3-O-phenyl; 3-Cl; 4-N(CH$_3$)$_2$; 4-N(CH$_2$CH$_3$)$_2$; 4-SO$_2$N(R')$_2$; 4-CN; 4-COOCH$_3$; 4-C(O)phenyl; 4-phenyl; 4-tert-butyl, 4-O-phenyl; 4-O-isopropyl; 4-OCH$_3$; 4-OCH$_2$CH$_3$; 4-O-n-butyl; 4-Cl; 4-Br; 4-F; 4-CH$_3$; 4-NO$_2$; 4-Cl; 3-NO$_2$, 4-morpholino; 3-NO$_2$, 2,5-dioxopyrrolidinyl, or 4-piperidinyl; and ii) $R^3$ is not any one or more of the following groups:

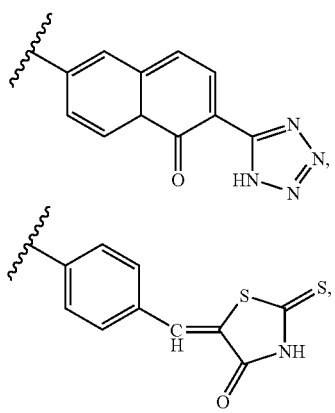

—CH=CH(thiophen-2-yl), —CH=CH-unsubstituted phenyl, —CH$_2$(3-NHCOPh-phenyl), -6-bromo-2-(4-ethylphenyl)-4-quinolinyl, —CH$_2$-pyrrolidine, unsubstituted cyclohexyl, unsubstituted benzyl, unsubstituted furan-2-yl, —CH=CH(3-NO$_2$-phenyl), —CH=CH(4-NO$_2$-phenyl), —CH$_2$-naphthyl, unsubstituted naphthyl, unsubstituted thiophene, unsubstituted cyclopropyl, 1,4-benzodioxin, 2-oxo-1-benzopyran, 4-oxo-1-benzopyran, 2-thienyl-quinolin-4-yl, 3-chloro-benzo[b]thiophen-2-yl, 5-Br-(thiophen-2-yl), 5-Cl-(thiophen-2-yl), 5-NO$_2$-(thiophen-2-yl), 5-NO$_2$-(furan-2-yl), 2,5-Cl-(thiophen-3-yl), —CH=CH-(5-NO$_2$-thiophen-2-yl), 5-NO$_2$-(benzothiophen-2-yl), 3-OCH$_3$-(naphth-2-yl), —CH$_2$O(2,4-Cl-phenyl), —(CH$_2$)$_2$S-phenyl, 2-phenyl-quinolin-4-yl, —CH$_2$O(4-Cl-phenyl), —CH$_2$CH$_2$-3-(4-Cl-phenyl)-1-phenyl-1-H-pyrazol-4-yl, or —CH$_2$(1,3-dioxoisoindole);

B) for compounds having the structure:

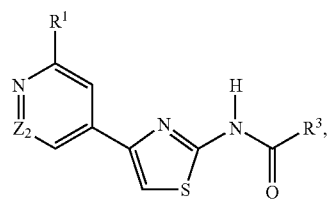

i) when $R^1$ is Cl, and $X_1$ is C—Cl, then $R^3$ is not NHSO$_2$-(2-CF$_3$-phenyl) or —NHSO$_2$-(2,6-dimethoxy-phenyl);

ii) when $R^1$ is CH$_3$, and $X_1$ is C—CH$_3$, then $R^3$ is not an optionally substituted indole or optionally substituted dihydroindole; and C) for compounds of general Formula I, when $Z_1$, $Z_2$ and $Z_3$ are each CH, $R^1$ is H, $X^1$ is CH and $X_2$ is C—COOCH$_3$, then $R^3$ is not 2-(4-ethyl-phenyl)-6-bromo-quinolin-4-yl; and III. for compounds described above where

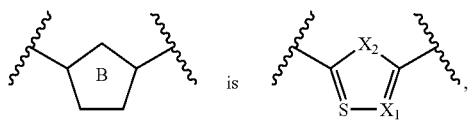

one or more of, or all of the following conditions apply:

A) when $Z^1$, $Z^2$ and $Z^3$ are each CH, $X^2$ is N, $X^1$ is CH, $Q^1$ is —CONR—, and $R^2$ is hydrogen or —CH$_3$, then $R^3$ is not optionally substituted pyridyl, optionally substituted thiazol-4-yl, —CH$_2$pyridyl, benzimidazol-4-yl, quinolin-2-yl, 1-bromo-isoquinolin-3-yl, benzthiazol-2-yl, optionally substituted 5,6,7,8-tetrahydro-naphthyridin-2-yl, or phenyl substituted with —CH$_2$piperidinyl; and B) when $Z^1$, $Z^2$ and $Z^3$ are each CH, $X^2$ is N, $X^1$ is CH, $Q^1$ is SO$_2$, and $R^2$ is hydrogen, then $R^3$ is not phenyl substituted with

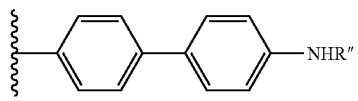

where R'' is hydrogen or —COCH$_3$;

C) when $Z^1$, $Z^2$ and $Z^3$ are each CH, $X_1$ is C—CO$_2$H, $X^2$ is CH, $R^2$ is hydrogen, and $Q^1$ is SO$_2$, then $R^3$ is not 2-CH$_3$-phenyl; and D) when $Z^1$, $Z^2$ and $Z^3$ are each CH, $X_1$ is CH, $X^2$ is N, $R^2$ is hydrogen, and $Q^1$ is CO, then $R^3$ is not 5-methoxy-6-trifluoromethyl-1H-indole.

The ROCK I kinase domain in the crystal or crystallizable composition may be any of residues 6-415 of SEQ ID NO:1, amino acid residues 6-405 of SEQ ID NO:1, amino acid residues 5-402 of SEQ ID NO:1, amino acid residues 5-401 of SEQ ID NO:1, or amino acid residues 6-401 of SEQ ID NO:1, or said kinase domain with conservative substitutions.

```
                                            SEQ ID NO: 1
          10         20         30         40
    MSTGDSFETR FEKMDNLLRD PKSEVNSDCL LDGLDALVYD 50         60         70         80
    LDFPALRKNK NIDNFLSRYK DTINKIRDLR MKAEDYEVVK 90        100        110        120
    VIGRGAFGEV QLVRHKSTRK VYAMKLLSKF EMIKRSDSAF 130        140        150        160
    FWEERDIMAF ANSPWVVQLF YAFQDDRYLY MVMEYMPGGD 170        180        190        200
    LVNLMSNYDV PEKWARFYTA EVVLALDAIH SMGFIHRDVK 210        220        230        240
    PDNMLLDKSG HLKLADFGTC MKMNKEGMVR CDTAVGTPDY 250        260        270        280
    ISPEVLKSQG GDGYYGRECD WWSVGVFLYE MLVGDTPFYA 290        300        310        320
    DSLVGTYSKI MNHKNSLTFP DDNDISKEAK NLICAFLTDR
```

```
                330        340        350        360
         EVRLGRNGVE EIKRHLFFKN DQWAWETLRD TVAPVVPDLS 370        380        390        400
         SDIDTSNFDD LEEDKGEEET FPIPKAFVGN QLPFVGFTYY 410        420        430        440
         SNRRYLSSAN PNDNRTSSNA DKSLQESLQK TIYKLEEQLH 450        460        470        480
         NEMQLKDEME QKCRTSNIKL DKIMKELDEE GNQRRNLEST 490        500        510        520
         VSQIEKEKML LQHRINEYQR KAEQENEKRR NVENEVSTLK 530        540        550        560
         DQLEDLKKVS QNSQLANEKL SQLQKQLEEA NDLLRTESDT 570        580        590        600
         AVRLRKSHTE MSKSISQLES LNRELQERNR ILENSKSQTD 610        620        630        640
         KDYYQLQAIL EAERRDRGHD SEMIGDLQAR ITSLQEEVKH 650        660        670        680
         LKHNLEKVEG ERKEAQDMLN HSEKEKNNLE IDLNYKLKSL 690        700        710        720
         QQRLEQEVNE HKVTKARLTD KHQSIEEAKS VAMCEMEKKL 730        740        750        760
         KEEREAREKA ENRVVQIEKQ CSMLDVDLKQ SQQKLEHLTG 770        780        790        800
         NKERMEDEVK NLTLQLEQES NKRLLLQNEL KTQAFEADNL 810        820        830        840
         KGLEKQMKQE INTLLEAKRL LEFELAQLTK QYRGNEGQMR 850        860        870        880
         ELQDQLEAEQ YFSTLYKTQV KELKEEIEEK NRENLKKIQE 890        900        910        920
         LQNEKETLAT QLDLAETKAE SEQLARGLLE EQYFELTQES 930        940        950        960
         KKAASRNRQE ITDKDHTVSR LEEANSMLTK DIEILRRENE 970        980        990       1000
         ELTEKMKKAE EEYKLEKEEE ISNLKAAFEK NINTERTLKT 1010       1020       1030       1040
         QAVNKLAEIM NRKDFKIDRK KANTQDLRKK EKENRKLQLE 1050       1060       1070       1080
         LNQEREKFNQ MVVKHQKELN DMQAQLVEEC AHRNELQMQL 1090       1100       1110       1120
         ASKESDIEQL RAKLLDLSDS TSVASFPSAD ETDGNLPESR 1130       1140       1150       1160
         IEGWLSVPNR GNIKRYGWKK QYVVVSSKKI LFYNDEQDKE 1170       1180       1190       1200
         QSNPSMVLDI DKLFHVRPVT QGDVYRAETE EIPKIFQILY 1210       1220       1230       1240
         ANEGECRKDV ALESLQTQKF TTKSDVWSFG VVLWELMTRG 1250       1260       1270       1280
         APPYPDVNTF HVFKPPPALE CRRCHVKCHR DHLDKKEDLI 1290       1300       1310       1320
         CPCKVSYDVT SARDMLLLAC SQDEQKKWVT HLVKKIPKNP 1330       1340       1350       1354
         PSGFVRASPR TLSTRSTANQ SFRKVVKNTS GKTS
```

The crystallizable composition may further comprise a crystallization solution containing 2-10% PEG, 100 mM buffer pH 5.0-6.0, 40-50 mM $CaCl_2$, 0-10 mM reducing agent, and 0-5% DMSO. Examples of PEG include, but are not limited to, PEG3350, PEG3000, PEG4000, and PEG6000. Buffers such as HEPES buffer, acetate buffer, sodium citrate buffer, MES buffer, bis-tris buffer may be used. One may also substitute the anions in $CaCl_2$ with another anion having −1 charge. Examples of reducing agents are DTT and β-mercaptoethanol. The crystal may be crystallized at 4-22° C. In one embodiment of this invention, the crystallizable composition comprises a crystallization solution of 2-8% PEG-3350, 100 mM buffer at pH 5.3-5.6, 40-50 mM $CaCl_2$, 0-10 mM DTT.

According to one embodiment, the invention provides a crystal with unit cell dimensions of a=b=179.6 to 184.8 Å, c=89.4 to 95 Å, α=β=90; and γ=120° and space group $P3_121$, with 2 molecules in the asymmetric unit. Preferably, the crystal comprises a human ROCK I-inhibitor complex. According to another embodiment, the invention provides a crystal with unit cell dimensions of a=b=182 Å, c=92 Å, α=β=90; and γ=120° and space group $P3_121$, with 2 molecules in the asymmetric unit. Preferably, the crystal comprises a human ROCK I-inhibitor complex.

It will be readily apparent to those skilled in the art that the unit cells of such a crystal composition may deviate up to ±1-3 Å from the above cell dimensions, depending on the deviation in the unit cell calculations or conformational change in the protein.

The ROCK I kinase domain or homologue thereof may be produced by any well-known method, including synthetic methods, such as solid phase, liquid phase and combination solid phase/liquid phase syntheses; recombinant DNA methods, including cDNA cloning, optionally combined with site directed mutagenesis; and/or purification of the natural products. In one embodiment of this invention, the protein is overexpressed in a baculovirus system.

Methods of Obtaining Crystals of ROCK I Kinase Domain, Complexes Thereof or Homologues Thereof This invention also relates to a method of obtaining a crystal of ROCK I kinase domain or homologue thereof, comprising the steps of:
 a) optionally producing and purifying a ROCK I kinase domain or homologue thereof;
 b) combining a crystallizable solution with said ROCK I kinase domain or homologue thereof to produce a crystallizable composition; and
 c) subjecting said crystallizable composition to conditions which promote crystallization and obtaining said crystal.

The invention also relates to a method of obtaining a crystal of a ROCK I kinase domain complex or ROCK I kinase domain homologue complex as described above, further comprising the step of:
 d) soaking said crystal in a buffer solution comprising a chemical entity.

In one embodiment, the buffer solution for soaking the crystal comprises about 500 μM to about 2 mM of compound and about 0-5% DMSO.

The invention also relates to a method of obtaining a crystal of ROCK I kinase domain complex or ROCK I kinase domain homologue complex, comprising the steps of:
 a) optionally producing and purifying a ROCK I kinase domain or homologue thereof;
 b) adding a chemical entity to a solution containing a ROCK I kinase domain or homologue thereof to form a complex;

c) combining a crystallizable solution with said ROCK I kinase domain complex or homologue thereof; and d) subjecting said crystallizable composition to conditions which promote crystallization to obtain said crystal.

In one embodiment, the concentration of the chemical entity in step b) is about 500 µM to about 2 mM. In one embodiment, the chemical entity is selected from the group consisting of an ATP analogue, nucleotide triphosphate, nucleotide diphosphate, nucleotide monophosphate, adenosine, inhibitor, substrate inhibitor, or active site inhibitor. In another embodiment, the crystallization solution is as described previously. In a further embodiment, the crystallizable composition is treated with micro-crystals of ROCK I kinase domain or ROCK I kinase domain complexes or homologues thereof.

In certain embodiments of this invention, the method of making crystals of ROCK I kinase domain complexes or homologues thereof includes the use of a device for promoting crystallization. Such devices can include, but are not limited to, hanging-drop, sitting-drop, dialysis or microtube batch devices. (See, U.S. Pat. Nos. 4,886,646, 5,096,676, 5,130,105, 5,221,410 and 5,400,741; Pav et al., *Proteins: Structure, Function, and Genetics* 20: 98-102 (1994), incorporated herein by reference). Hanging-drop, sitting-drop, and some adaptations of the microbatch methods (D'Arcy et al., *J. Cryst. Growth* 168: 175-180 (1996) and Chayen, *J. Appl. Cryst.* 30: 198-202 (1997)) produce crystals by vapor diffusion. The hanging drop and sitting drop containing the crystallizable composition is equilibrated in a reservoir containing a higher or lower concentration of the precipitant. As the drop approaches equilibrium with the reservoir, the saturation of protein in the solution leads to the formation of crystals.

Microseeding or seeding may be used to increase the size and quality of crystals. In this instance, micro-crystals are crushed to yield a stock seed solution. The stock seed solution is diluted in series. Using a needle, glass rod, micro-pipet, micro-loop or strand of hair, a small sample from each diluted solution is added to a set of equilibrated drops containing a protein concentration equal to or less than a concentration needed to create crystals without the presence of seeds. The aim is to end up with a single seed crystal that will act to nucleate crystal growth in the drop.

It will be readily apparent to one of skill in the art to vary the above-described crystallization conditions to identify other crystallization conditions that would produce crystals of a ROCK I kinase domain homologue, a ROCK I kinase domain homologue complex, a ROCK I kinase domain, or other ROCK I kinase domain complexes. Such variations include, but are not limited to, adjusting pH, protein concentration and/or crystallization temperature, changing the identity or concentration of salt and/or precipitant used, using a different method of crystallization, or introducing additives such as detergents (e.g., TWEEN 20 (monolaurate), LDAO, Brij 30 (4 lauryl ether)), sugars (e.g., glucose, maltose), organic compounds (e.g., dioxane, dimethylformamide), lanthanide ions, or polyionic compounds that aid in crystallization. High throughput crystallization assays may also be used to assist in finding or optimizing the crystallization condition.

In certain embodiments, the crystal comprising a ROCK I kinase domain, ROCK I kinase domain complex or homologue thereof diffracts X-rays to a resolution of at least 2.6 Å. In other embodiments, the crystal comprising a ROCK I kinase domain, ROCK I kinase domain complex or homologues thereof diffract X-rays to a resolution of at least 5.0 Å, at least 3.5 Å, at least 3.2 Å, at least 3.0 Å, or at least 2.9 Å.

In certain embodiments, the crystal comprising a ROCK I kinase domain, ROCK I kinase domain complex or homologue thereof can produce an electron density map having resolution of at least 2.6 Å. In other embodiments, the crystal comprising a ROCK I kinase domain, ROCK I kinase domain complex or homologue thereof can produce an electron density map having resolution of at least 5.0 Å, at least 3.5 Å, at least 3.2 Å, at least 3.0 Å, or at least 2.9 Å.

In certain embodiments, the electron density map produced above is sufficient to determine the atomic coordinates of a ROCK I kinase domain, ROCK I kinase domain complex, or homologue thereof.

Binding Pockets of ROCK I Kinase Domain or Homologue Thereof

The present invention provides the three-dimensional X-ray structure of ROCK I-inhibitor complexes. The atomic coordinates for the structures of ROCK I-inhibitor complexes are presented in Table 2, 3, 4, or 5.

To use the structure coordinates generated for the ROCK I complex or one of its binding pockets or homologue thereof, it may be necessary to convert the structure coordinates, or portions thereof, into a three-dimensional shape (i.e., a three-dimensional representation of these complexes or binding pockets). This is achieved through the use of a computer and commercially available software that is capable of generating the three-dimensional representations or structures of molecules or molecular complexes, or portions thereof, from a set of structural coordinates. These three-dimensional representations may be displayed on a computer screen.

Binding pockets, also referred to as binding sites in the present invention, are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or part of the binding pocket. An understanding of such associations will help lead to the design of drugs having more favorable associations with their target receptor or enzyme, and thus, improved biological effects. Therefore, this information is valuable in designing potential inhibitors of the binding pockets of biologically important targets. The binding pockets of this invention will be useful and important for drug design.

The conformations of ROCK I and other proteins at a particular amino acid site, along the polypeptide backbone, can be compared using well-known procedures for performing sequence alignments of the amino acids. Such sequence alignments allow for the equivalent sites on these proteins to be compared. Such methods for performing sequence alignment include, but are not limited to, the "bestfit" program and CLUSTAL W Alignment Tool, Higgins et al., supra.

Figure 2A:
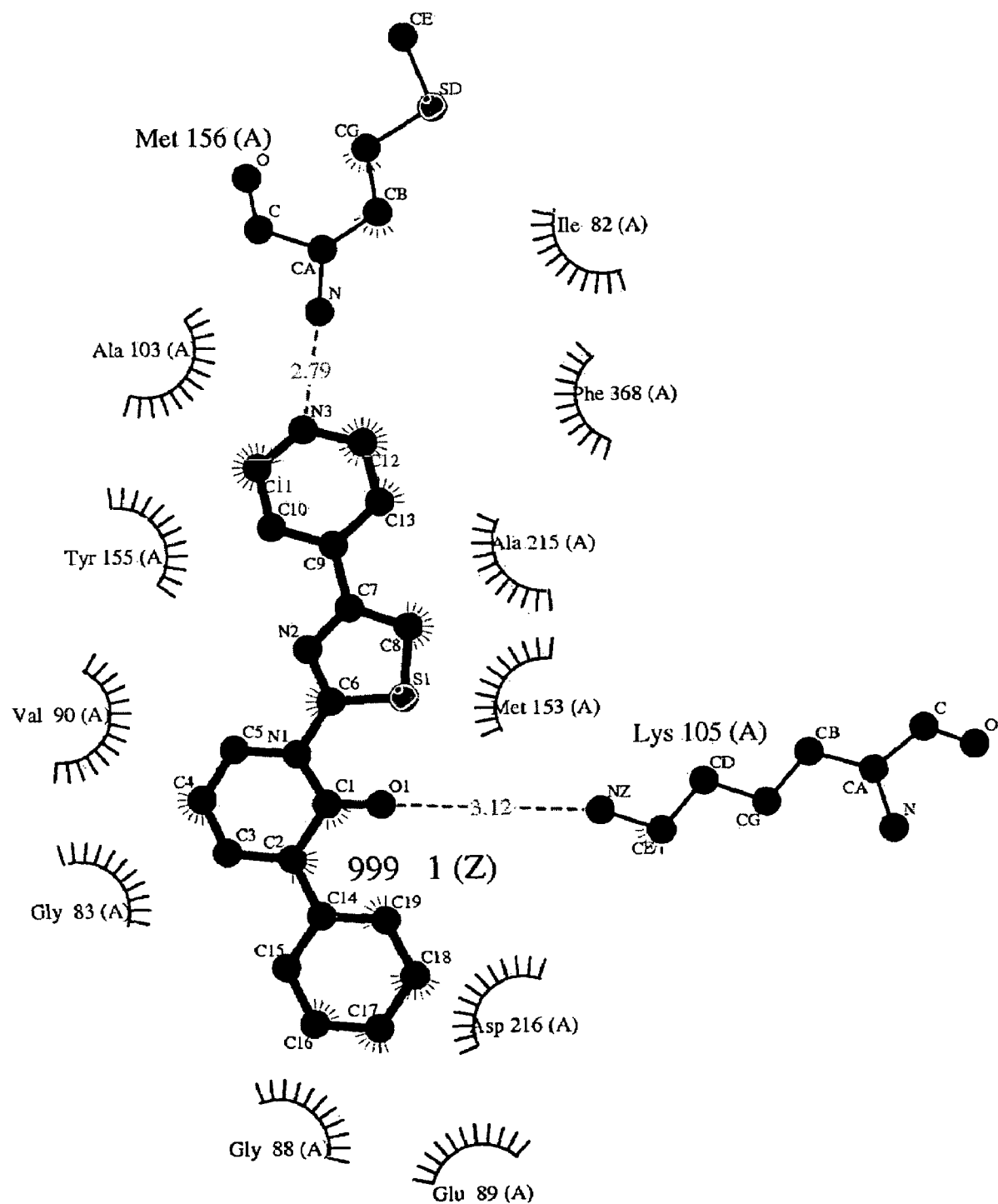
FIG. 2A shows a detailed representation of the active site of ROCK I with inhibitor2.
Figure 2B:
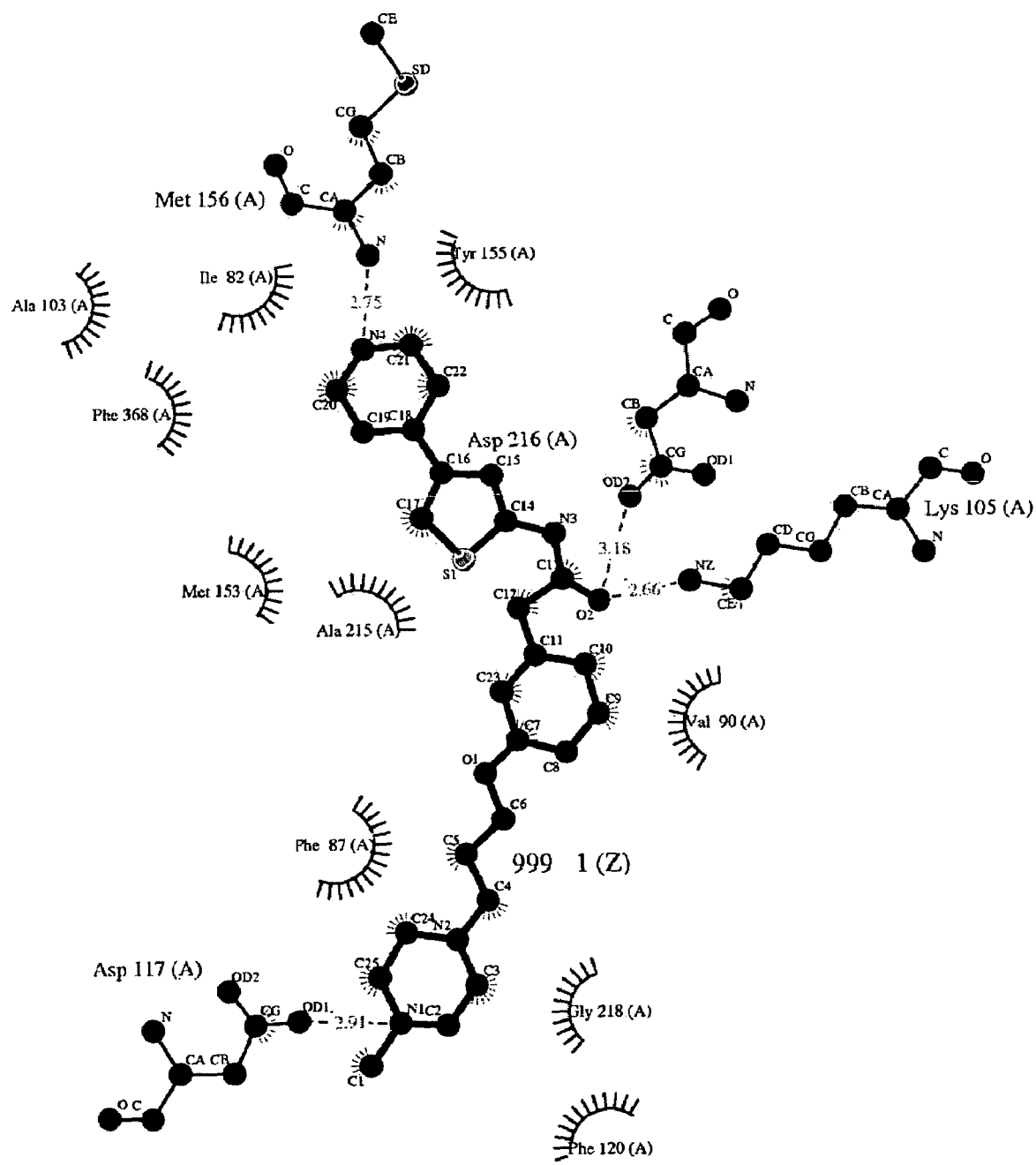
FIG. 2B shows a detailed representation of the active site of ROCK I with inhibitor3.
Figure 2C:
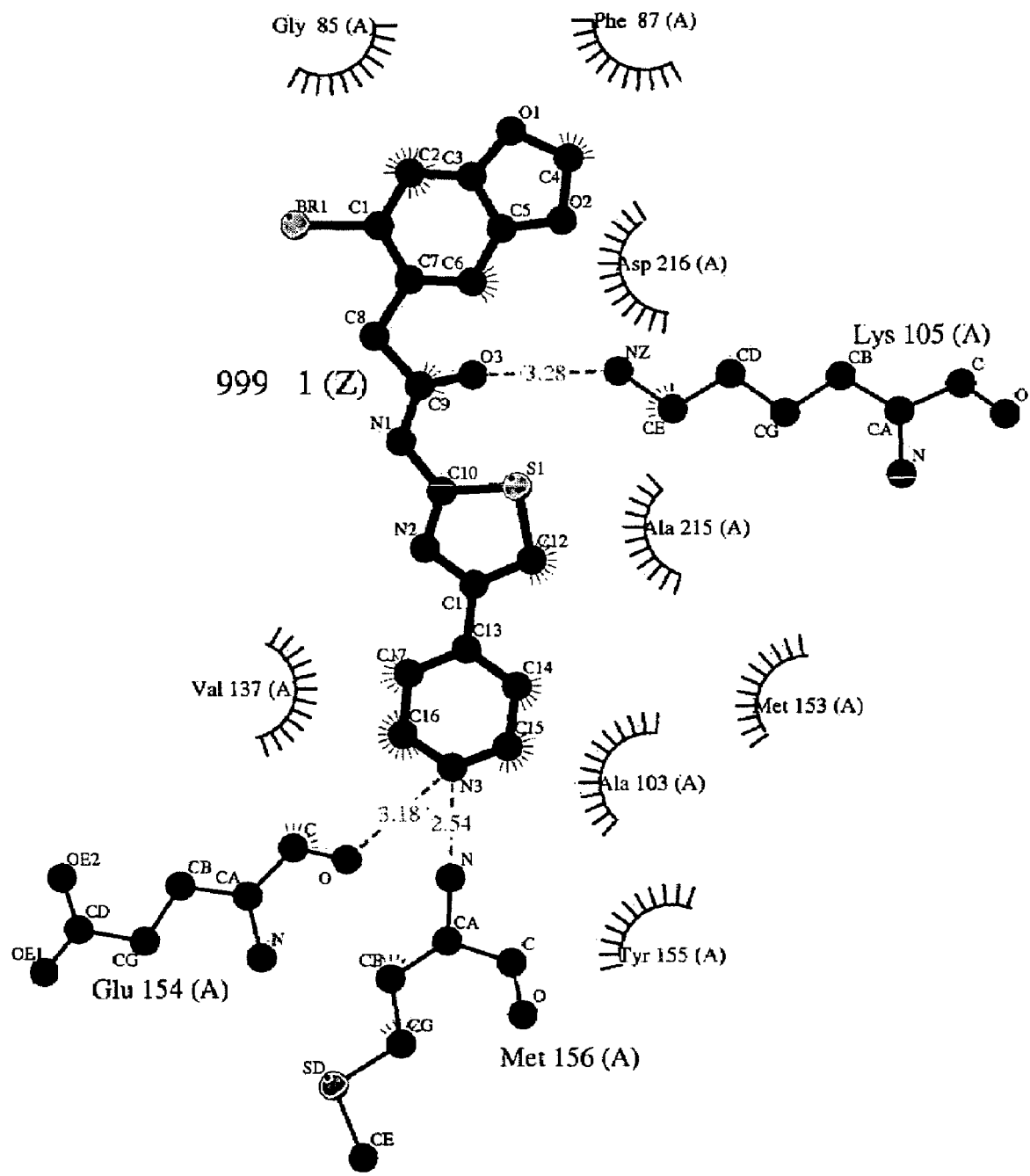
FIG. 2C shows a detailed representation of the active site of ROCK I with inhibitor4.
Figure 2D:
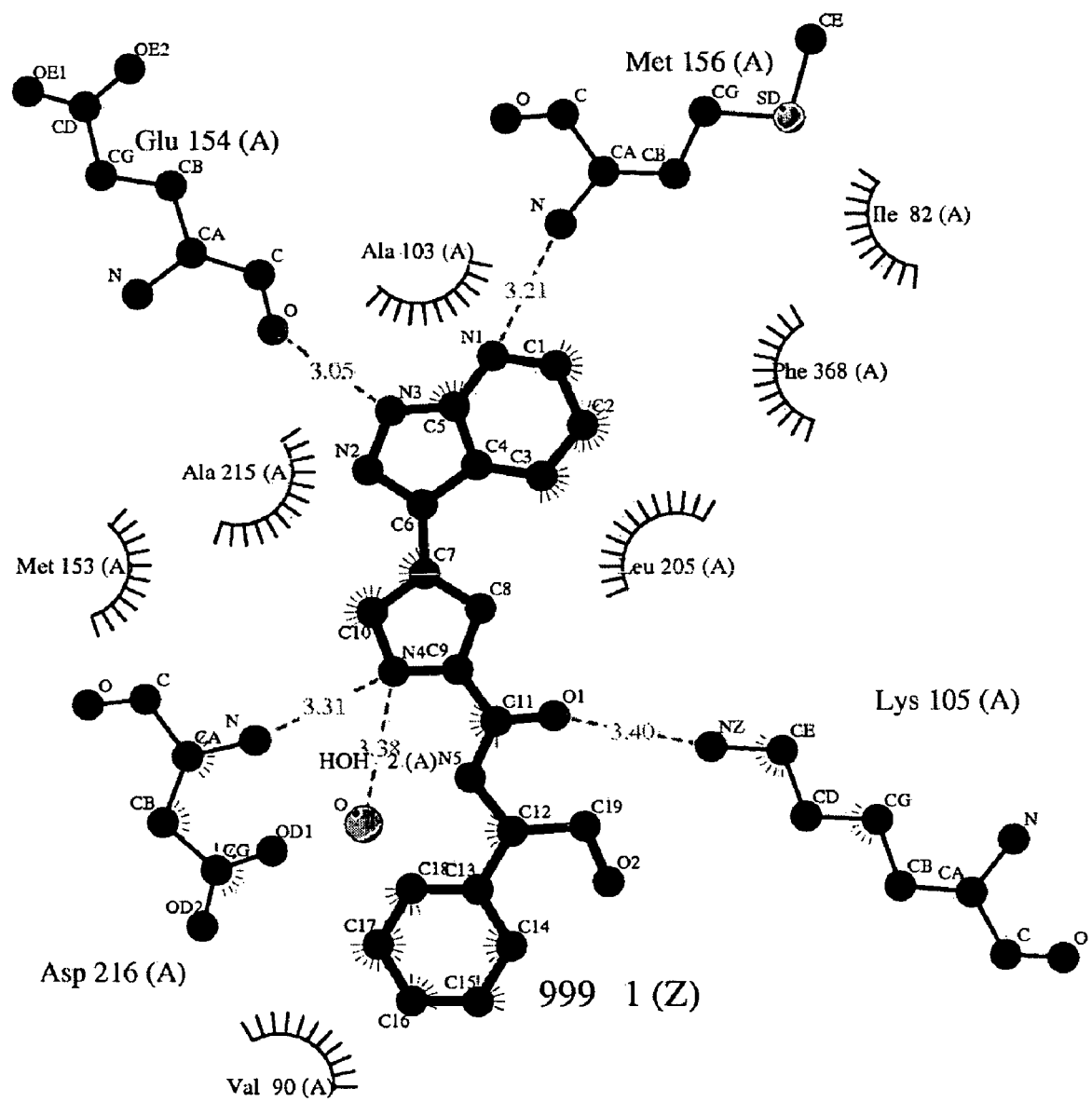
FIG. 2D shows a detailed representation of the active site of ROCK I with inhibitor5.

FIGS. 2A and 2B show a detailed representation of the active site of ROCK I-inhibitor4 complex and ROCK I-inhibitor5 complex, respectively.

In one embodiment, the inhibitor-binding pocket comprises amino acid residues I82, G83, G85, A86, G88, E89, V90, A103, K105, M153, E154, Y155, M156, A215, D216, and F368, according to the structure of the ROCK I-inhibitor2 complex in Table 2. These amino acid residues are within 4 Å ("4 Å sphere of amino acids") of inhibitor2 in the inhibitor-binding pocket as identified using the program CONTACT from the CCP4 program.

In an alternate embodiment, the inhibitor-binding pocket comprises amino acid residues I82, R84, F87, G88, V90, A103, K105, L107, D117, F120, E124, M153, E154, Y155, M156, L205, A215, D216, G218 and F368, according to the structure of the ROCK I-inhibitor3 complex in Table 3. These amino acid residues are within 4 Å ("4 Å sphere of amino acids") of inhibitor3 in the inhibitor-binding pocket as identified using the program CONTACT from the CCP4 program.

In another embodiment, the inhibitor-binding pocket comprises amino acid residues G83, G85, F87, G88, E89, V90, A103, K105, L107, V137, M153, E154, Y155, M156, A215, and D216, according to the structure of the ROCK I-inhibitor4 complex in Table 4. These amino acid residues are within 4 Å ("4 Å sphere of amino acids") of inhibitor4 in the inhibitor-binding pocket as identified using the program CONTACT from the CCP4 program.

In yet another embodiment, the inhibitor-binding pocket comprises amino acid residues I82, R84, G85, V90, A103, K105, L107, V137, M153, E154, Y155, M156, L205, A215, D216 and F368, according to the structure of the ROCK I-inhibitor5 complex in Table 5. These amino acid residues are within 4 Å ("4 Å sphere of amino acids") of inhibitor5 in the inhibitor-binding pocket as identified using the program CONTACT from the CCP4 program.

In one embodiment, the inhibitor-binding pocket comprises amino acid residues Val90, Ala103, Lys105, Met153, Glu154, Tyr155, Met156, Ala215, and Asp216, according to any one of Table 2, 3, 4, or 5.

In one embodiment, the inhibitor-binding pocket comprises amino acid residues Ile82, Gly83, Arg84, Gly85, Ala86, Phe87, Gly88, Glu89, Val 90, Ala103, Lys105, Leu107, Asp117, Phe120, Glu124, Val137, Met153, Glu154, Tyr155, Met156, Leu205, Ala215, Asp216, Gly218, and Phe368, according to any one of Table 2, 3, 4, or 5.

In one embodiment, the inhibitor-binding pocket comprises amino acid residues Ile82, Gly83, Arg84, Gly85, Ala86, Phe87, Gly88, Glu89, Val90, Gln91, Leu92, Tyr102, Ala103, Met104, Lys105, Leu106, Leu107, Ser108, Met112, Arg115, Asp117, Ser118, Ala119, Phe120, Phe121, Glu124, Met128, Val137, Gln138, Met151, Val152, Met153, Glu154, Tyr155, Met156, Pro157, Gly158, Gly159, Asp160, Arg197, Lys200, Asp202, Asn203, Leu205, Leu206, Lys213, Leu214, Ala215, Asp216, Phe217, Gly218, Thr219, Cys220, Met221, Asp232, Thr233, Ala234, Val235, Gly236, and Phe368, according to the structure of the ROCK I-inhibitor3 complex in Table 3. These amino acid residues are within 8 Å ("8 Å sphere of amino acids") of inhibitor3 in the inhibitor-binding pocket, as identified using the program CONTACT from the CCP4 program.

It will be readily apparent to those of skill in the art that the numbering of amino acid residues in homologues of human ROCK I may be different than that set forth for human ROCK I. Corresponding amino acids in ROCK I homologues are easily identified by visual inspection of the amino acid sequences or by using commercially available homology software programs. Homologues of ROCK I include, for example, ROCK I from other species, such as non-human primates, mouse, rat, etc.

Those of skill in the art understand that a set of structure coordinates for an enzyme or an enzyme-complex, or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The variations in coordinates discussed above may be generated due to mathematical manipulations of the ROCK I-inhibitor structure coordinates. For example, the structure coordinates set forth in Table 2, 3, 4, or 5 may undergo crystallographic permutations of the structure coordinates, fractionalization of the structure coordinates, integer additions or subtractions to sets of the structure coordinates, inversion of the structure coordinates, or any combination of the above.

Alternatively, modifications in the crystal structure due to mutations, additions, substitutions, and/or deletions of amino acids, or other changes in any of the components that make up the crystal, may also account for variations in structure coordinates. If such variations are within a certain root mean square deviation as compared to the original coordinates, the resulting three-dimensional shape is considered encompassed by this invention. Thus, for example, a ligand that bound to the inhibitor-binding pocket of ROCK I would also be expected to bind to another binding pocket whose structure coordinates defined a shape that fell within the RMSD value.

Various computational analyses may be necessary to determine whether a molecule or binding pocket, or portion thereof, is sufficiently similar to the binding pockets above-described. Such analyses may be carried out in well known software applications, such as ProFit (A. C. R. Martin, ProFit version 1.8, http://www.bioinf.org.uk/software), Swiss-Pdb Viewer (Guex and Peitsch, *Electrophoresis* 18: 2714-2723 (1997)), the Molecular Similarity application of QUANTA (Accelrys, San Diego, Calif. © 2001, 2002) and as described in the accompanying User's Guide, which are incorporated herein by reference.

The above programs permit comparisons between different structures, different conformations of the same structure, and different parts of the same structure. The procedure used in QUANTA (Accelrys, San Diego, Calif. ©2001, 2002) and Swiss-Pdb Viewer (Guex and Peitsch, *Electrophoresis* 18: 2714-2723 (1997) to compare structures is divided into four steps: 1) loading of the structures to be compared; 2) defining the atom equivalences in these structures; 3) performing a fitting operation on the structures; and 4) analyzing the results.

The procedure used in ProFit to compare structures includes the following steps: 1) loading the structures to be compared; 2) specifying selected residues of interest; 3) defining the atom equivalences in the selected residues; 4) performing a fitting operation on the selected residues; and 5) analyzing the results.

Each structure in the comparison is identified by a name. One structure is identified as the target (i.e., the fixed structure); all remaining structures are working structures (i.e., moving structures). Since atom equivalency within QUANTA (Accelrys, San Diego, Calif. ©2001, 2002) is defined by user input, for the purposes of this invention, we will define equivalent atoms as protein backbone atoms N, O, C and Cα for all corresponding amino acid residues between two structures being compared.

The corresponding amino acids may be identified by sequence alignment programs such as the "bestfit" program available from the Genetics Computer Group which uses the local homology algorithm described by Smith and Waterman in *Advances in Applied Mathematics* 2: 482 (1981), which is incorporated herein by reference. A suitable amino acid sequence alignment will require that the proteins being aligned share minimum percentage of identical amino acids. Generally, a first protein being aligned with a second protein should share in excess of about 35% identical amino acids (Hanks et al., *Science* 241: 42 (1988); Hanks and Quinn, *Methods in Enzymology* 200: 38 (1991)). The identification of equivalent residues can also be assisted by secondary structure alignment, for example, aligning the α-helices, β-sheets in the structure. The program Swiss-Pdb viewer (Guex and Peitsch, *Electrophoresis* 18: 2714-2723 (1997) utilizes a best fit algorithm that is based on secondary sequence alignment.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by the above programs. The Swiss-Pdb Viewer program (Guex and Peitsch, *Electrophoresis* 18: 2714-2723 (1997) sets an RMSD cutoff for eliminating pairs of equivalent atoms that have high RMSD values. An RMSD cutoff value can be used to exclude pairs of equivalent atoms with extreme individual RMSD values. In the program ProFit, the RMSD cutoff value can be specified by the user.

For the purpose of this invention, any molecule, molecular complex, binding pocket, motif, domain thereof or portion thereof that is within a root mean square deviation for backbone atoms (N, Cα, C, O) when superimposed on the relevant backbone atoms described by structure coordinates listed in Table 2, 3, 4, or 5 is encompassed by this invention.

One embodiment of this invention provides a crystalline molecule comprising a domain defined by structure coordinates of a set of amino acid residues that are identical to ROCK I amino acid residues according to Table 2, 3, 4, or 5, wherein the RMSD between said set of amino acid residues and said ROCK I amino acid residues is not more than about 3.0 Å. In other embodiments, the RMSD between said set of amino acid residues and said ROCK I amino acid residues is not greater than about 2.0 Å, not greater than about 1.0 Å, or not greater than about 0.5 Å.

In one embodiment, the present invention provides a crystalline molecule comprising all or part of a binding pocket defined by a set of amino acid residues which are identical to human ROCK I amino acid residues Val90, Ala103, Lys105, Met153, Glu154, Tyr155, Met156, Ala215, and Asp216 according to any one of Table 2, 3, 4, or 5, wherein the RMSD of the backbone atoms between said human ROCK I amino acid residues and said set of amino acid residues which are identical is not greater than about 1.5 Å. In other embodiments, the RMSD is not greater than about 1.0 Å, 0.8 Å, 0.5 Å, 0.3 Å, or 0.2 Å.

In one embodiment, the present invention provides a crystalline molecule comprising all or part of a binding pocket defined by a set of amino acid residues which are identical to human ROCK I amino acid residues Ile82, Gly83, Arg84, Gly85, Ala86, Phe87, Gly88, Glu89, Val 90, Ala103, Lys105, Leu107, Asp117, Phe120, Glu124, Val137, Met153, Glu154, Tyr155, Met156, Leu205, Ala215, Asp216, Gly218, and Phe368, according to any one of Table 2, 3, 4, or 5, wherein the RMSD of the backbone atoms between said human ROCK I amino acid residues and said set of amino acid residues which are identical is not greater than about 1.5 Å. In other embodiments, the RMSD is not greater than about 1.0 Å, 0.8 Å, 0.5 Å, 0.3 Å, or 0.2 Å.

In one embodiment, the present invention provides a crystalline molecule comprising all or part of a binding pocket defined by a set of amino acid residues which are identical to human ROCK I amino acid residues Ile82, Gly83, Arg84, Gly85, Ala86, Phe87, Gly88, Glu89, Val90, Gln91, Leu92, Tyr102, Ala103, Met104, Lys105, Leu106, Leu107, Ser108, Met112, Arg115, Asp117, Ser118, Ala119, Phe120, Phe121, Glu124, Met128, Val137, Gln138, Met151, Val152, Met153, Glu154, Tyr155, Met156, Pro157, Gly158, Gly159, Asp160, Arg197, Lys200, Asp202, Asn203, Leu205, Leu206, Lys213, Leu214, Ala215, Asp216, Phe217, Gly218, Thr219, Cys220, Met221, Asp232, Thr233, Ala234, Val235, Gly236, and Phe368 according to Table 3, wherein the RMSD of the backbone atoms between said human ROCK I amino acid residues and said set of amino acid residues which are identical is not greater than about 1.5 Å. In other embodiments, the RMSD is not greater than about 1.0 Å, 0.8 Å, 0.5 Å, 0.3 Å, or 0.2 Å.

Computer Systems

According to an alternate embodiment, this invention provides a machine-readable data storage medium, comprising a data storage material encoded with machine-readable data, wherein said data define any one of the above-mentioned molecules, molecular complexes or binding pockets thereof. In one embodiment, the data define the above-mentioned binding pockets by comprising the structure coordinates of said amino acid residues according to any one of Table 2, 3, 4, or 5. To use the structure coordinates generated for ROCK I, homologues thereof, or one of its binding pockets, it is at times necessary to convert them into a three-dimensional shape or to extract three-dimensional structural information from them. This is achieved through the use of commercially or publicly available software that is capable of generating a three-dimensional structure or a three-dimensional representation of molecules or portions thereof from a set of structure coordinates. In one embodiment, three-dimensional structure or representation may be displayed graphically.

Therefore, according to another embodiment, this invention provides a machine-readable data storage medium comprising a data storage material encoded with machine readable data. In one embodiment, a machine programmed with instructions for using said data is capable of generating a three-dimensional structure or three-dimensional representation of any of the molecules, or molecular complexes or binding pockets thereof, that are described herein.

This invention also provides a computer comprising:
(a) a machine-readable data storage medium, comprising a data storage material encoded with machine-readable data, wherein said data define any one of the above-described molecules or molecular complexes;
(b) a working memory for storing instructions for processing said machine-readable data;
(c) a central processing unit (CPU) coupled to said working memory and to said machine-readable data storage medium for processing said machine readable data and means for generating three-dimensional structural information of said molecule or molecular complex; and
(d) output hardware coupled to said central processing unit for outputting three-dimensional structural information of said molecule or molecular complex, or information produced by using said three-dimensional structural information of said molecule or molecular complex.

In one embodiment, the data define the binding pocket of the molecule or molecular complex.

Three-dimensional data generation may be provided by an instruction or set of instructions, such as a computer program or commands for generating a three-dimensional structure or graphical representation from structure coordinates, or by subtracting distances between atoms, calculating chemical energies for a ROCK I molecule or molecular complex or homologues thereof, or calculating or minimizing energies for an association of a ROCK I molecule or molecular complex or homologues thereof to a chemical entity. The graphical representation can be generated or displayed by commercially available software programs. Examples of software programs include but are not limited to QUANTA (Accelrys, San Diego, Calif. ©2001, 2002), O (Jones et al., *Acta Crystallogr.* A47: 110-119 (1991)), and RIBBONS (Carson, *J. Appl. Crystallogr.* 24: 958-961 (1991)), which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described in the Rational Drug Design section.

Information regarding said binding pocket or information produced by using said binding pocket can be outputted through display terminals, touchscreens, facsimile machines, modems, CD-ROMs, printers, a CD or DVD recorder, ZIP™ or JAZ™ drives, or disk drives. The information can be in graphical or alphanumeric form.

In one embodiment, the computer executes an instruction such as a computer program for generating three-dimensional structure or docking. In another embodiment, the computer further comprises a commercially available software program to display the information as a graphical representation. Examples of software programs include but are not limited to, QUANTA (Accelrys, San Diego, Calif. ©2001, 2002), O (Jones et al., *Acta Crystallogr.* A47: 110-119 (1991)), and RIBBONS (Carson, *J. Appl. Crystallogr.* 24: 958-961 (1991)), all of which are incorporated herein by reference.

Figure 3:
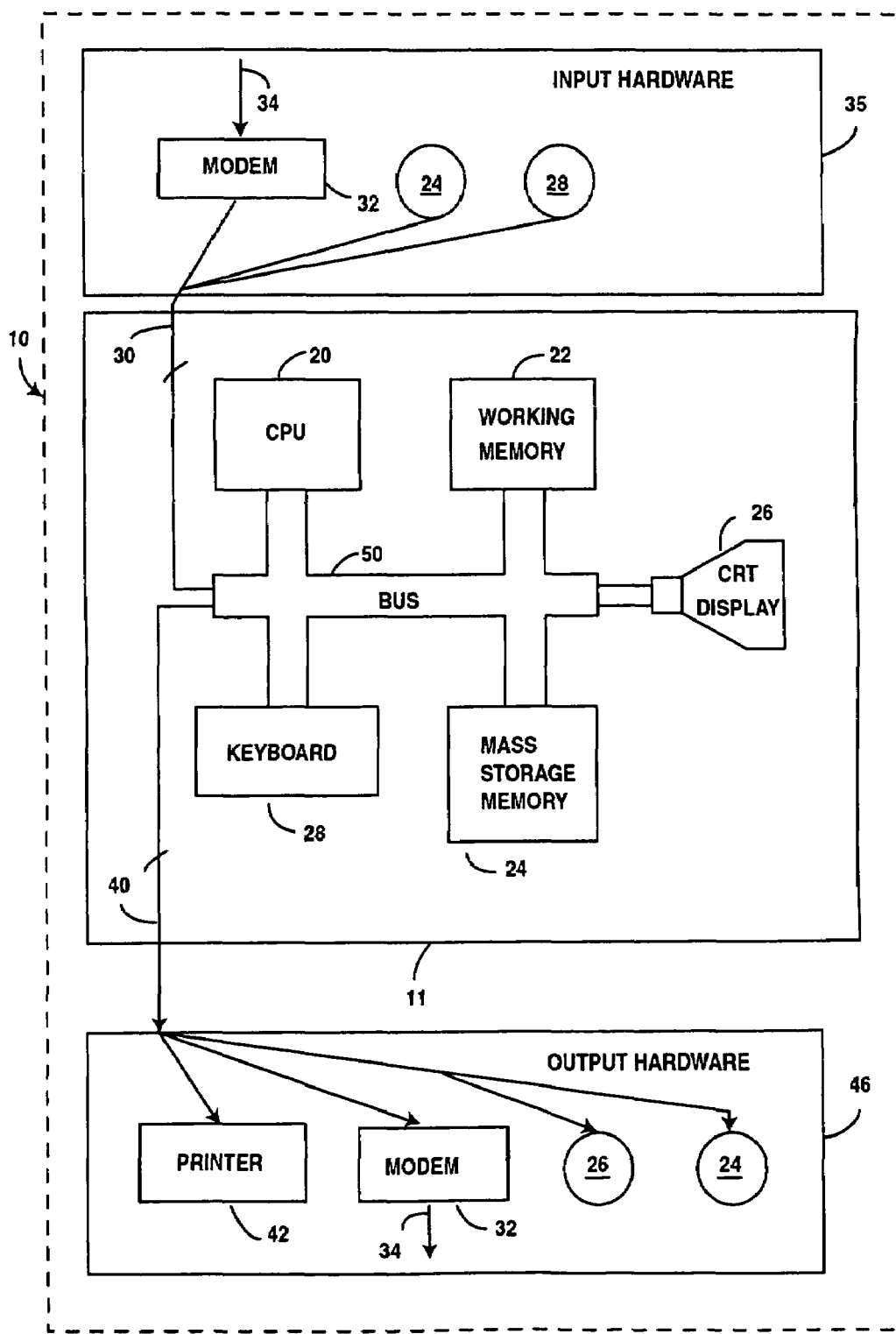
FIG. 3 shows a diagram of a system used to carry out the instructions encoded by the storage medium of FIGS. 4 and 5.

FIG. 3 demonstrates one version of these embodiments. System (10) includes a computer (11) comprising a central processing unit ("CPU") (20), a working memory (22) which may be, e.g., RAM (random-access memory) or "core" memory, mass storage memory (24) (such as one or more disk drives, CD-ROM drives or DVD-ROM drives), one or more cathode-ray tube ("CRT") display terminals (26), one or more keyboards (28), one or more input lines (30), and one or more output lines (40), all of which are interconnected by a conventional bi-directional system bus (50).

Input hardware (35), coupled to computer (11) by input lines (30), may be implemented in a variety of ways. Machine-readable data of this invention may be inputted via the use of a modem or modems (32) connected by a telephone line or dedicated data line (34). Alternatively or additionally, the input hardware (35) may comprise CD-ROM, DVD-ROM, or disk drives (24). In conjunction with display terminal (26), keyboard (28) may also be used as an input device.

Output hardware (46), coupled to computer (11) by output lines (40), may similarly be implemented by conventional devices. By way of example, output hardware (46) may include CRT display terminal (26) for displaying a graphical representation of a binding pocket of this invention using a program such as QUANTA (Accelrys, San Diego, Calif. ©2001, 2002), as described herein. Output hardware may also include a printer (42), so that hard copy output may be produced, or a disk drive (24) to store system output for later use. Output hardware may also include a display terminal, touchscreens, facsimile machines, modems, a CD or DVD recorder, ZIP™ or JAZ™ drives, disk drives, or other machine-readable data storage device.

In operation, CPU (20) coordinates the use of the various input and output devices (35) and (46), coordinates data access from mass storage (24) and data transfer to and from working memory (22), and determines the sequence of data processing steps. A number of programs may be used to process the machine-readable data of this invention. Such programs are discussed in reference to the computational methods of drug discovery as described herein. Specific references to components of the hardware system (10) are included as appropriate throughout the following description of the data storage medium.

Figure 4:
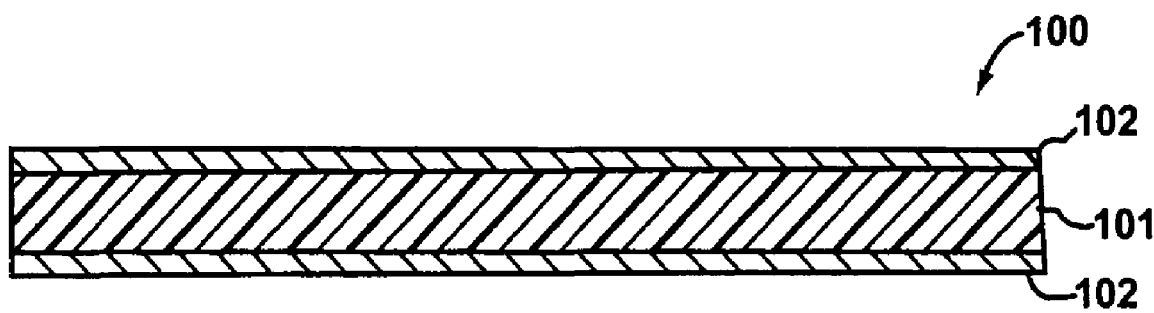
FIG. 4 shows a cross section of a magnetic storage medium.

FIG. 4 shows a cross section of a magnetic data storage medium (100), which can be encoded with a machine-readable data that can be carried out by a system, such as system (10) of FIG. 3. Medium (100) can be a conventional floppy diskette or hard disk, having a suitable substrate (101), which may be conventional, and a suitable coating (102), which may be conventional, on one or both sides, containing magnetic domains (not visible) whose polarity or orientation can be altered magnetically. Medium (100) may also have an opening (not shown) for receiving the spindle of a disk drive or other data storage device (24).

The magnetic domains of coating (102) of medium (100) may be polarized or oriented so as to encode conventional, machine readable data, such as that described herein, for execution by a system such as system (10) of FIG. 3.

Figure 5:
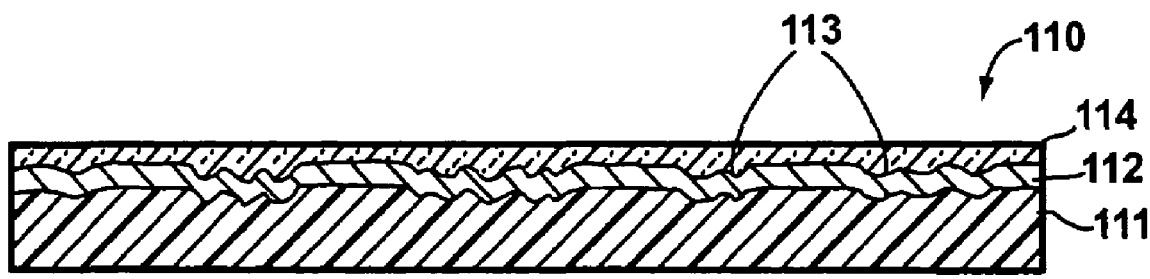
FIG. 5 shows a cross section of a optically-readable data storage medium.

FIG. 5 shows a cross section of an optically-readable data storage medium (110), which also can be encoded with machine-readable data or a set of instructions that can be carried out by a system such as system (10) of FIG. 3. Medium (110) can be a conventional compact disk read only memory (CD-ROM) or a rewritable medium, such as a magneto-optical disk which is optically readable and magneto-optically writable. Medium (100) preferably has a suitable substrate (111), which may be conventional, and a suitable coating (112), which may be conventional, usually on one side of substrate (111).

In the case of CD-ROM, as is well known, coating (112) is reflective and is impressed with a plurality of pits (113) to encode the machine-readable data. The arrangement of pits is read by reflecting laser light off the surface of coating (112). A protective coating (114), which preferably is substantially transparent, is provided on top of coating (112).

In the case of a magneto-optical disk, as is well known, coating (112) has no pits (113), but has a plurality of magnetic domains whose polarity or orientation can be changed magnetically when heated above a certain temperature, as by a laser (not shown). The orientation of the domains can be read by measuring the polarization of laser light reflected from coating (112). The arrangement of the domains encodes the data as described above.

In one embodiment, the structure coordinates of said molecules or molecular complexes are produced by homology modeling of at least a portion of the structure coordinates of Table 2, 3, 4, or 5. Homology modeling can be used to generate structural models of ROCK I homologues or other homologous proteins based on the known structure of ROCK I. This can be achieved by performing one or more of the following steps: performing sequence alignment between the amino acid sequence of a molecule (possibly an unknown molecule) against the amino acid sequence of ROCK I; identifying conserved and variable regions by sequence or structure; generating structure coordinates for structurally conserved residues of the unknown structure from those of ROCK I; generating conformations for the structurally variable residues in the unknown structure; replacing the non-conserved residues of ROCK I with residues in the unknown structure; building side chain conformations; and refining and/or evaluating the unknown structure.

Software programs that are useful in homology modeling include XALIGN (Wishart et al., *Comput. Appl. Biosci.* 10: 687-688 (1994)) and CLUSTAL W Alignment Tool, Higgins et al., supra. See also, U.S. Pat. No. 5,884,230. These references are incorporated herein by reference.

To perform the sequence alignment, programs such as the "bestfit" program available from the Genetics Computer Group (Waterman in *Advances in Applied Mathematics* 2: 482 (1981), which is incorporated herein by reference) and CLUSTAL W Alignment Tool (Higgins et al., supra, which is incorporated by reference) can be used. To model the amino acid side chains of homologous molecules, the amino acid residues in ROCK I can be replaced, using a computer graphics program such as "O" (Jones et al., *Acta Cryst. Sect. A* 47: 110-119 (1997)), by those of the homologous protein, where they differ. The same orientation or a different orientation of the amino acid can be used. Insertions and deletions of amino acid residues may be necessary where gaps occur in the sequence alignment. However, certain portions of the active site of ROCK I and its homologues are highly conserved with essentially no insertions and deletions.

Homology modeling can be performed using, for example, the computer programs SWISS-MODEL available through Glaxo Wellcome Experimental Research in Geneva, Switzerland; WHATIF available on EMBL servers; Schnare et al., *J. Mol. Biol.* 256: 701-719 (1996); Blundell et al., *Nature* 326: 347-352 (1987); Fetrow and Bryant, *Bio/Technology* 11: 479-484 (1993); Greer, *Methods in Enzymology* 202: 239-252 (1991); and Johnson et al., *Crit. Rev. Biochem. Mol. Biol.* 29: 1-68 (1994). An example of homology modeling can be found, for example, in Szklarz, *Life Sci.* 61: 2507-2520 (1997). These references are incorporated herein by reference.

Thus, in accordance with the present invention, data capable of generating the three-dimensional structure or three-dimensional representation of the above-described molecules or molecular complexes, or binding pockets thereof, can be stored in a machine-readable storage medium, which is capable of displaying structural information or a graphical three-dimensional representation of the structure. In one embodiment, means of generating three-dimensional information are provided by means for generating a three-dimensional structural representation of the binding pocket or domain of a molecule or molecular complex.

Rational Drug Design

The ROCK I structure coordinates or the three-dimensional graphical representation generated from these coordinates may be used in conjunction with a computer for a variety of purposes, including drug discovery.

For example, the structure encoded by the data may be computationally evaluated for its ability to associate with chemical entities. Chemical entities that associate with ROCK I may inhibit or activate ROCK I or its homologues, and therefore are potential drug candidates. Alternatively, the structure encoded by the data may be displayed in a graphical three-dimensional representation on a computer screen. This allows visual inspection of the structure, as well as visual inspection of the structure's association with chemical entities.

In the following embodiments, the invention provides methods for using the ROCK or ROCK-like domain and binding pockets described herein. In one embodiment, the invention provides a method of using a computer for selecting an orientation of a chemical entity that interacts favorably with a binding pocket or domain comprising the steps of:

(a) providing the structure coordinates of said binding pocket or domain to a computer comprising the means for generating three-dimensional structural information from said structure coordinates;

(b) employing computational means to dock a first chemical entity in all or part of the binding pocket or domain;

(c) quantifying the association between said first chemical entity and all or part of the binding pocket or domain for different orientations of the chemical entity; and (d) selecting the orientation of said first chemical entity with the most favorable interaction based on said quantified association.

In one embodiment, the docking is facilitated by said quantified association.

In another embodiment, the above-described method further comprises the following steps before step (a):

(e) producing a crystal of a molecule or molecular complex comprising ROCK I kinase domain or homologue thereof;

(f) determining the three-dimensional structure coordinates of the molecule or molecular complex by X-ray diffraction of the crystal; and (g) identifying a binding pocket that corresponds to said binding pocket.

Three-dimensional structural information in the methods recited herein, such as, for example, step (a) of the above-described method, may be generated by instructions, such as a computer program or commands that can generate a three-dimensional representation; subtract distances between atoms; calculate chemical energies for a ROCK I molecule, molecular complex, or homologues thereof; or calculate and/or minimize the chemical energies of an association of ROCK I molecule, molecular complex, or homologues thereof to a chemical entity. These types of computer programs are known in the art. The graphical representation can be generated or displayed by commercially available software programs. Examples of software programs include but are not limited to QUANTA (Accelrys, San Diego, Calif. ©2001, 2002), O (Jones et al., *Acta Crystallogr*. A47: 110-119 (1991)), and RIBBONS (Carson, *J. Appl. Crystallogr*. 24: 958-961 (1991)), which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described below.

Any of the computer programs or procedures described herein may be used in the computational means of the methods recited herein, such as, for example, step (b) of the method described above.

The above method of paragraph 125 may further comprise the following step after step (d): outputting said quantified association to a suitable output hardware, such as a CRT display terminal, a CD or DVD recorder, ZIP™ or JAZ™ drive, a disk drive, or other machine-readable data storage device, as described previously. The method may further comprise generating a three-dimensional structure, graphical representation thereof, or both, of the binding pocket or domain prior to step (b).

One embodiment of this invention provides for any of the above methods, wherein energy minimization, molecular dynamics simulations, or rigid body minimizations are performed simultaneously with or following step (b).

Any of the above methods may further comprise the steps of:

(e) repeating steps (b) through (d) with a second chemical entity, wherein the second chemical entity is different from the first chemical entity; and (f) selecting said first or second chemical entity based on said most favorable interaction.

In another embodiment, the invention provides a method of using a computer for selecting an orientation of a chemical entity with a favorable shape complementarity in a binding pocket comprising the steps of:

(a) providing the structure coordinates of said binding pocket and all or part of the ligand bound therein to a computer comprising the means for generating three-dimensional structural information from said structure coordinates;

(b) employing computational means to dock a first chemical entity in all or part of the binding pocket;

(c) quantitating the contact score of said first chemical entity in different orientations in the binding pocket; and (d) selecting an orientation with the highest contact score.

In one embodiment, the docking is monitored and directed or facilitated by the contact score.

The above-described methods may further comprise the step of generating a three-dimensional graphical representation of the binding pocket and all or part of the ligand bound therein prior to step (b).

The above-described methods may further comprise the steps of:

(e) repeating steps (b) through (d) with a second chemical entity, wherein the second chemical entity is different from the first chemical entity; and (f) selecting at said first or second chemical entity based on said highest contact score.

In another embodiment, the invention provides a method for screening a plurality of chemical entities to associate at a deformation energy of binding of not greater than 7 kcal/mol with said binding pocket comprising the steps of:

(a) employing computational means, which utilizes structure coordinates of said binding pocket to dock one of said plurality of chemical entities in all or part of said binding pocket;

(b) quantifying the deformation energy of binding between the chemical entity and all or part of the binding pocket;

(c) repeating steps (a) and (b) for each remaining chemical entity; and (d) outputting a set of chemical entities that associate with all or part of the binding pocket at a deformation energy of binding of not greater than 7 kcal/mol to a suitable output hardware.

In another embodiment, the present invention provides a method comprising the steps of:

(a) constructing a computer model of a binding pocket of a molecule or molecular complex;

(b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of a ROCK I kinase domain, or homologue thereof to produce said chemical entity;

(c) employing computational means to dock said chemical entity to be evaluated in all or part of said binding pocket, thereby providing an energy-minimized configuration of said chemical entity in all or part of the binding pocket; and (d) evaluating said energy-minimized configuration.

In one embodiment, the above-described method may further comprise the steps of:

(e) synthesizing said chemical entity; and (f) contacting said chemical entity with said molecule or molecular complex to determine the ability of said chemical entity to activate or inhibit said molecule.

Alternatively, the structure coordinates of the ROCK I binding pockets may be utilized in a method for identifying a candidate inhibitor of a molecule or molecular complex comprising a binding pocket of ROCK I. This method comprises the steps of:

(a) using a three-dimensional structure of the binding pocket or domain to design, select or optimize a plurality of chemical entities;

(b) contacting each chemical entity with the molecule or molecular complex;

(c) assessing the inhibitory effect on the catalytic activity of the molecule or molecular complex by the chemical entity; and (d) selecting a chemical entity based on the effect of the chemical entity on the activity of the molecule or molecular complex.

In one embodiment of the invention, using a three-dimensional structure of the binding pocket or domain to design, select or optimize a plurality of chemical entities in step (a) of the above-described method is employing computational means to generate a group of one or more chemical entities based on calculated interactions between said chemical entities and a ROCK I binding pocket or domain.

In the above-described methods, activity may be monitored by an assay as shown in Example 10.

In one embodiment of the above-described method, the three-dimensional structure of the binding pocket or domain is displayed as a graphical representation.

In an alternate embodiment, the present invention provides a method of designing a compound or complex that associates with all or part of the binding pocket or domain comprising the steps of:

(a) providing the structure coordinates of said binding pocket or domain to a computer comprising the means for generating three-dimensional structural information from said structure coordinates;

(b) using the computer to dock a first chemical entity in part of the binding pocket or domain;

(c) docking a second chemical entity in another part of the binding pocket or domain, wherein the second chemical entity is different from the first chemical entity;

(d) quantifying the association between the first and second chemical entity and part of the binding pocket or domain;

(e) repeating steps (b) to (d) with another first and second chemical entity, selecting a first and a second chemical entity based on said quantified association of both of said first and second chemical entity;

(f) selecting a first and a second chemical entity based on said association of said first and second chemical entity quantified in steps (d) and (e);

(g) optionally, visually inspecting the relationship of the selected first and second chemical entity to each other in relation to the binding pocket or domain on a computer screen using the three-dimensional graphical representation of the binding pocket or domain and said selected first and second chemical entity; and (h) assembling the selected first and second chemical entity into a compound or complex that interacts with said binding pocket by model building.

In yet another embodiment, the invention provides a method for identifying a candidate inhibitor that interacts with a binding site of a human Rho-kinase I kinase domain or a homologue thereof, comprising the steps of:

(a) obtaining a crystal comprising a human Rho-kinase I kinase domain or homologue thereof;

(b) obtaining the structure coordinates of amino acids of the crystal obtained in step (a);

(c) generating a three-dimensional structure of the human Rho-kinase I kinase domain or homologue thereof using the structure coordinates of the amino acids obtained in step (b) with a root mean square deviation from backbone atoms of said amino acids of not more than ±3.0 Å;

(d) determining a binding site of the human Rho-kinase I kinase domain or homologue thereof from said three-dimensional structure; and (e) performing docking to identify the candidate inhibitor.

The above-described method may further comprise the step of:

(f) contacting the identified candidate inhibitor with the human Rho-kinase I kinase domain or homologue thereof in order to determine the effect of the inhibitor on catalytic activity.

In yet another embodiment, the invention provides a method for identifying a candidate inhibitor that interacts with a binding site of a human Rho-kinase I kinase domain or a homologue thereof, comprising the steps of: (a) determining a binding site from a three-dimensional structure of the human Rho-kinase I kinase domain or homologue thereof; and (b) designing or identifying the candidate inhibitor which interacts with said binding site.

In one embodiment of the above-described methods, the binding site of the human Rho-kinase I kinase domain or homologue thereof comprises the structure coordinates of Val90, Ala103, Lys105, Met153, Glu154, Tyr155, Met156, Ala215, and Asp216 according to any one of Table 2, 3, 4, or 5, wherein the root mean square deviation from the backbone atoms of said amino acids is not more than ±1.5 Å.

In one embodiment of the above-described methods, the binding site of human Rho-kinase I kinase domain or homologue thereof comprises the structure coordinates of Ile82, Gly83, Arg84, Gly85, Ala86, Phe87, Gly88, Glu89, Val 90, Ala103, Lys105, Leu107, Asp117, Phe120, Glu124, Val137, Met153, Glu154, Tyr155, Met156, Leu205, Ala215, Asp216, Gly218, and Phe368 according to any one of Table 2, 3, 4, or 5, wherein the root mean square deviation from the backbone atoms of said amino acids is not more than ±1.5 Å.

In one embodiment of the above-described methods, the binding site of the human Rho-kinase I kinase domain or homologue thereof comprises the structure coordinates of Ile82, Gly83, Arg84, Gly85, Ala86, Phe87, Gly88, Glu89, Val90, Gln91, Leu92, Tyr102, Ala103, Met104, Lys105, Leu106, Leu107, Ser108, Met112, Arg115, Asp117, Ser118, Ala119, Phe120, Phe121, Glu124, Met128, Val137, Gln138, Met151, Val152, Met153, Glu154, Tyr155, Met156, Pro157, Gly158, Gly159, Asp160, Arg197, Lys200, Asp202, Asn203, Leu205, Leu206, Lys213, Leu214, Ala215, Asp216, Phe217, Gly218, Thr219, Cys220, Met221, Asp232, Thr233, Ala234, Val235, Gly236, and Phe368 according to Table 3, wherein the root mean square deviation from the backbone atoms of said amino acids is not more than ±1.5 Å.

In one embodiment of the above-described methods, the structure coordinates of the amino acids are according to any one of Table 2, 3, 4, or 5±a root mean square deviation from the backbone atoms of said amino acids of not more than 3.0 Å.

In one embodiment of the above-described methods, the crystal is a human Rho-kinase I kinase domain with or without an active site inhibitor. In one embodiment, the crystal belongs to space group P3$_1$21 and has unit cell parameters of a=b=180.9, c=91.5.

In another embodiment, the invention provides a method for identifying a candidate inhibitor of a molecule or molecular complex comprising a binding pocket or domain comprising amino acid residues selected from the group consisting of:

(i) a set of amino acid residues which are identical to human Rho-kinase I amino acid residues Val90, Ala103, Lys105, Met153, Glu154, Tyr155, Met156, Ala215, and Asp216 according to any one of Table 2, 3, 4, or 5, wherein the root mean square deviation of the backbone atoms between said set of amino acid residues and said human Rho-kinase I amino acid residues which are identical is not greater than about 1.5 Å;

(ii) a set of amino acid residues which are identical to human Rho-kinase I amino acid residues Ile82, Gly83, Arg84, Gly85, Ala86, Phe87, Gly88, Glu89, Val 90, Ala103, Lys105, Leu107, Asp117, Phe120, Glu124, Val137, Met153, Glu154, Tyr155, Met156, Leu205, Ala215, Asp216, Gly218, and Phe368 according to any one of Table 2, 3, 4, or 5, wherein the root mean square deviation of the backbone atoms between said set of amino acid residues and said human Rho-kinase I amino acid residues which are identical is not greater than about 1.5 Å;

(iii) a set of amino acid residues which are identical to human Rho-kinase I amino acid residues Ile82, Gly83, Arg84, Gly85, Ala86, Phe87, Gly88, Glu89, Val90, Gln91, Leu92, Tyr102, Ala103, Met104, Lys105, Leu106, Leu107, Ser108, Met112, Arg115, Asp117, Ser118, Ala119, Phe120, Phe121, Glu124, Met128, Val137, Gln138, Met151, Val152, Met153, Glu154, Tyr155, Met156, Pro157, Gly158, Gly159, Asp160, Arg197, Lys200, Asp202, Asn203, Leu205, Leu206, Lys213, Leu214, Ala215, Asp216, Phe217, Gly218, Thr219, Cys220, Met221, Asp232, Thr233, Ala234, Val235, Gly236, and Phe368 according to Table 3, wherein the root mean square deviation of the backbone atoms between said set of amino acid residues and said human Rho-kinase I amino acid residues which are identical is not greater than about 1.5 Å; and (iv) a set of amino acid residues that are identical to human Rho-kinase I amino acid residues according to any one of Table 2, 3, 4, or 5, wherein the root mean square deviation between said set of amino acid residues and said human Rho-kinase I amino acid residues is not more than about 3 Å;

comprising the steps of:

(a) using a three-dimensional structure of all or part of the binding pocket or domain to design, select or optimize a plurality of chemical entities; and (b) selecting said candidate inhibitor from said chemical entities based on the inhibitory effect of said chemical entities on the catalytic activity of the molecule or molecular complex.

In yet another embodiment, the invention provides a method of using the crystal compositions of this invention in an inhibitor screening assay comprising the steps of:

(a) selecting a potential inhibitor by performing rational drug design with a three-dimensional structure determined for the crystal, wherein said selecting is performed in conjunction with computer modeling;

(b) contacting the potential inhibitor with a kinase; and (c) detecting the ability of the potential inhibitor for inhibiting the kinase.

For the first time, the present invention permits the use of molecular design techniques to identify, select and design chemical entities, including inhibitory compounds, capable of binding to ROCK I or ROCK I-like binding pockets, motifs and domains.

Elucidation of binding pockets on ROCK I according to the present invention provides the necessary information for designing new chemical entities and compounds that may interact with ROCK I substrate, active site, in whole or in part.

Throughout this section, discussions about the ability of a chemical entity to bind to, interact with or inhibit ROCK I binding pockets refer to features of the entity alone.

The design of compounds that bind to or inhibit ROCK I binding pockets according to this invention generally involves consideration of two factors. First, the chemical entity must be capable of physically and structurally associating with parts or all of the ROCK I binding pockets. Non-covalent molecular interactions important in this association include hydrogen bonding, van der Waals interactions, hydrophobic interactions and electrostatic interactions.

Second, the chemical entity must be able to assume a conformation that allows it to associate with the ROCK I binding pockets directly. Although certain portions of the chemical entity will not directly participate in these associations, those portions of the chemical entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of a chemical entity comprising several chemical entities that directly interact with the ROCK I or ROCK I-like binding pockets.

The potential inhibitory or binding effect of a chemical entity on ROCK I binding pockets may be analyzed prior to its actual synthesis and testing by the use of computer modeling techniques. If the theoretical structure of the given entity suggests insufficient interaction and association between it and the ROCK I binding pockets, testing of the entity is obviated. However, if computer modeling indicates a strong interaction, the molecule may then be synthesized and tested for its ability to bind to a ROCK I binding pocket. This may be achieved by testing the ability of the molecule to inhibit ROCK I using the assays described in Example 10.

A potential inhibitor of a ROCK I binding pocket may be computationally evaluated by a series of steps in which chemical entities or fragments are screened and selected for their ability to associate with the ROCK I binding pockets.

One skilled in the art may use one of several methods to screen chemical entities or fragments or moieties thereof for their ability to associate with the binding pockets described herein. This process may begin by visual inspection of, for example, any of the binding pockets on the computer screen based on the ROCK I structure coordinates according to any one of Table 2, 3, 4, or 5, or other coordinates which define a similar shape generated from the machine-readable storage medium. Selected chemical entities, or fragments or moieties thereof may then be positioned in a variety of orientations, or docked, within that binding pocket as defined supra. Docking may be accomplished using software such as QUANTA (Accelrys, San Diego, Calif. ©2001, 2002) and Sybyl (Tripos Associates, St. Louis, Mo.), followed by, or performed simultaneously with, energy minimization, rigid-body minimization (Gshwend, supra) and molecular dynamics with standard molecular mechanics force fields, such as CHARMM and AMBER.

Specialized computer programs may also assist in the process of selecting fragments or chemical entities. These include:

1. GRID (Goodford, P. J., "A Computational Procedure for Determining Energetically Favorable Binding Sites on Biologically Important Macromolecules", *J. Med. Chem.* 28: 849-857 (1985)). GRID is available from Oxford University, Oxford, UK.
2. MCSS (Miranker et al., "Functionality Maps of Binding Sites: A Multiple Copy Simultaneous Search Method." *Proteins Struct. Funct. Genet.* 11: 29-34 (1991)). MCSS is available from Molecular Simulations, San Diego, Calif.
3. AUTODOCK (Goodsell et al., "Automated Docking of Substrates to Proteins by Simulated Annealing", *Proteins Struct. Funct. and Genet.* 8: 195-202 (1990)). AUTODOCK is available from Scripps Research Institute, La Jolla, Calif.
4. DOCK (Kuntz et al., "A Geometric Approach to Macromolecule-Ligand Interactions", *J. Mol. Biol.* 161: 269-288 (1982)). DOCK is available from University of California, San Francisco, Calif.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of ROCK I. This would be followed by manual model building using software such as QUANTA (Accelrys, San Diego, Calif. ©2001, 2002) or Sybyl (Tripos Associates, St. Louis, Mo.).

Useful programs to aid one of skill in the art in connecting the individual chemical entities or fragments include:

1. CAVEAT (Bartlett et al., "CAVEAT: A Program to Facilitate the Structure-Derived Design of Biologically Active Molecules", in *Molecular Recognition in Chemical and Biological Problems*, S. M. Roberts, Ed., Royal Society of Chemistry, Special Publication No. 78: 182-196 (1989); Lauri, G. and Bartlett, P. A., "CAVEAT: A Program to Facilitate the Design of Organic Molecules", *J. Comp. Aid. Molec. Design* 8: 51-66 (1994)). CAVEAT is available from the University of California, Berkeley, Calif.
2. 3D Database systems such as ISIS (MDL Information Systems, San Leandro, Calif.). This area is reviewed in Martin, Y. C., "3D Database Searching in Drug Design", *J. Med. Chem.* 35: 2145-2154 (1992).
3. HOOK (Eisen et al., "HOOK: A Program for Finding Novel Molecular Architectures that Satisfy the Chemical and Steric Requirements of a Macromolecule Binding Site", *Proteins Struct. Funct. Genet.* 19: 199-221 (1994)). HOOK is available from Molecular Simulations, San Diego, Calif.

Instead of proceeding to build an inhibitor of a ROCK I binding pocket in a step-wise fashion one fragment or chemical entity at a time as described above, inhibitory or other ROCK I binding compounds may be designed as a whole or "de novo" using either an empty binding pocket or, optionally, including some portion(s) of a known inhibitor(s). There are many de novo ligand design methods including:

1. LUDI (Böhm, H.-J., "The Computer Program LUDI: A New Method for the De Novo Design of Enzyme Inhibitors", *J. Comp. Aid. Molec. Design* 6: 61-78 (1992)). LUDI is available from Molecular Simulations Incorporated, San Diego, Calif.
2. LEGEND (Nishibata et al., *Tetrahedron* 47: 8985-8990 (1991)). LEGEND is available from Molecular Simulations Incorporated, San Diego, Calif.
3. LeapFrog (available from Tripos Associates, St. Louis, Mo.).
4. SPROUT (Gillet et al., "SPROUT: A Program for Structure Generation)", *J. Comp. Aid. Molec. Design* 7: 127-153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry, *J. Med. Chem.* 33: 883-894 (1990); see also, Navia, M. A. and Murcko, M. A., "The Use of Structural Information in Drug Design", Current Opinions in Structural Biology 2: 202-210 (1992); Balbes et al., "A Perspective of Modern Methods in Computer-Aided Drug Design", in *Reviews in Computational Chemistry*, K. B. Lipkowitz and D. B. Boyd, Eds., VCH Publishers, New York, 5: 337-379 (1994); see also, Guida, W. C., "Software For Structure-Based Drug Design", *Curr. Opin. Struct. Biology* 4: 777-781 (1994)).

Once a chemical entity has been designed or selected by the above-described methods, the efficiency with which that entity may bind to any of the above binding pockets may be tested and optimized by computational evaluation. For example, an effective binding pocket inhibitor must preferably demonstrate a relatively small difference in energy between its bound and free states (i.e., a small deformation energy of binding). Thus, the most efficient binding pocket inhibitors should preferably be designed with a magnitude of deformation energy of binding of not greater than about 10 kcal/mole, more preferably, not greater than 7 kcal/mole. Binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

A chemical entity designed or selected based on its binding to any one of the above-described binding pockets may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. ©1995); AMBER, version 4.1 (P. A. Kollman, University of California at San Francisco, ©1995); QUANTA/CHARMM (Accelrys, San Diego, Calif. ©2001, 2002); Insight II/Discover (Molecular Simulations, Inc., San Diego, Calif. ©1998); DelPhi (Molecular Simulations, Inc., San Diego, Calif. ©1998); and AMSOL (Quantum Chemistry Program Exchange, Indiana University). These programs may be implemented, for instance, using a Silicon Graphics workstation such as an Indigo2 with "IMPACT" graphics. Other hardware systems and software packages will be known to those skilled in the art.

Another approach enabled by this invention is the computational screening of small molecule databases for chemical entities or compounds that can bind in whole, or in part, to any of the above binding pocket. In this screening, the quality of fit of such entities to the binding pocket may be judged either by shape complementarity or by estimated interaction energy (Meng et al., *J. Comp. Chem.* 13: 505-524 (1992)).

According to another embodiment, the invention provides chemical entities which associate with a ROCK I binding pocket produced or identified by the method set forth above.

Another particularly useful drug design technique enabled by this invention is iterative drug design. Iterative drug design is a method for optimizing associations between a protein and a chemical entity by determining and evaluating the three-dimensional structures of successive sets of protein/chemical entity complexes.

In iterative drug design, crystals of a series of protein or protein complexes are obtained and then the three-dimensional structures of each crystal is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

In some cases, iterative drug design is carried out by forming successive protein-compound complexes and then crystallizing each new complex. High throughput crystallization assays may be used to find a new crystallization condition or to optimize the original protein crystallization condition for the new complex. Alternatively, a pre-formed protein crystal may be soaked in the presence of an inhibitor, thereby forming a protein/compound complex and obviating the need to crystallize each individual protein/compound complex.

Any of the above-described methods may be used to design peptide or small molecule mimics of a ligand which may have inhibitory effects on full-length ROCK I protein or fragments thereof, or on full-length ROCK I protein which is mutated, or fragments of the mutated protein thereof.

Structure Determination of Other Molecules

The structure coordinates set forth in Table 2, 3, 4, or 5 can also be used in obtaining structural information about other crystallized molecules or molecular complexes. This may be achieved by any of a number of well-known techniques, including molecular replacement.

According to one embodiment on this invention, the machine-readable data storage medium comprises a data storage material encoded with a first set of machine readable data which comprises the Fourier transform of at least a portion of the structure coordinates set forth in Table 2, 3, 4, or 5 or homology model thereof, and which, when using a machine programmed with instructions for using said data, can be combined with a second set of machine readable data comprising the X-ray diffraction pattern of a molecule or molecular complex to determine at least a portion of the structure coordinates corresponding to the second set of machine readable data.

In another embodiment, the invention provides a computer for determining at least a portion of the structure coordinates corresponding to X-ray diffraction data obtained from a molecule or molecular complex having an unknown structure, wherein said computer comprises:

(a) a machine-readable data storage medium comprising a data storage material encoded with machine-readable data, wherein said data comprises at least a portion of the structure coordinates of ROCK I according to any one of Table 2, 3, 4, or 5 or a homology model thereof;

(b) a machine-readable data storage medium comprising a data storage material encoded with machine-readable data, wherein said data comprises X-ray diffraction data obtained from said molecule or molecular complex having an unknown structure; and (c) instructions for performing a Fourier transform of the machine-readable data of (a) and for processing said machine-readable data of (b) into structure coordinates.

For example, the Fourier transform of at least a portion of the structure coordinates set forth in any one of Table 2, 3, 4, or 5, or a homology model thereof, may be used to determine at least a portion of the structure coordinates of the molecule or molecular complex.

Therefore, in another embodiment, this invention provides a method of utilizing molecular replacement to obtain structural information about a molecule or a molecular complex of unknown structure, wherein the molecule or molecular complex is sufficiently homologous to ROCK I kinase domain, comprising the steps of:

(a) crystallizing said molecule or molecular complex of unknown structure;

(b) generating X-ray diffraction data from said crystallized molecule or molecular complex;

(c) applying at least a portion of the ROCK I structure coordinates set forth in any one of Table 2, 3, 4, or 5, or a homology model thereof, to the X-ray diffraction data to generate a three-dimensional electron density map of at least a portion of the molecule or molecular complex whose structure is unknown; and (d) generating a structural model of the molecule or molecular complex from the three-dimensional electron density map.

In one embodiment, the method is performed using a computer. In another embodiment, the molecule is selected from the group consisting of ROCK I kinase domain, a ROCK I kinase domain homologue, ROCK I protein or a homologue thereof. In another embodiment, the molecular complex is a ROCK I kinase domain complex, a ROCK I kinase domain homologue complex, ROCK I protein complex or a homologue thereof.

By using molecular replacement, all or part of the structure coordinates of ROCK I as provided by this invention (and set forth in Table 2, 3, 4, or 5) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of ROCK I kinase domain according to any one of Table 2, 3, 4, or 5 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions", in *Meth. Enzymol.* 115: 55-77 (1985); M. G. Rossmann, ed., "The Molecular Replacement Method", Int. Sci. Rev. Ser. No. 13, Gordon & Breach, New York (1972)).

The structure of any portion of any crystallized molecule or molecular complex that is sufficiently homologous to any portion of the structure of human ROCK I kinase domain can be resolved by this method.

In one embodiment, the method of molecular replacement is utilized to obtain structural information about a ROCK I kinase domain homologue. The structure coordinates of ROCK I kinase domain as provided by this invention are particularly useful in solving the structure of ROCK I kinase domain complexes that are bound by ligands, substrates and inhibitors.

Furthermore, the structure coordinates of ROCK I kinase domain as provided by this invention are useful in solving the structure of ROCK I kinase domains that have amino acid substitutions, additions and/or deletions (referred to collectively as "ROCK I kinase domain mutants", as compared to naturally occurring ROCK I). These ROCK I kinase domain mutants may optionally be crystallized in co-complex with a chemical entity. The crystal structures of a series of such complexes may then be solved by molecular replacement and compared with that of wild-type ROCK I. Potential sites for modification within the various binding pockets of the enzyme may thus be identified. This information provides an additional tool for determining the most efficient binding interactions, for example, increased hydrophobic interactions, between ROCK I and a chemical entity or compound.

The structure coordinates are also particularly useful in solving the structure of crystals of the kinase domain of ROCK I or homologues co-complexed with a variety of chemical entities. This approach enables the determination of the optimal sites for interaction between chemical entities, including candidate ROCK I inhibitors. For example, high resolution X-ray diffraction data collected from crystals exposed to different types of solvent allows the determination of where each type of solvent molecule resides. Small molecules that bind tightly to those sites can then be designed and synthesized and tested for their ROCK I inhibition activity.

All of the complexes referred to above may be studied using well-known X-ray diffraction techniques and may be refined using 1.5-3.4 Å resolution X-ray data to an R value of about 0.30 or less using computer software, such as X-PLOR (Yale University, ©1992, distributed by Molecular Simulations, Inc.; see, e.g., Blundell & Johnson, supra; *Meth. Enzymol.* vol. 114 & 115, H. W. Wyckoff et al., eds., Academic Press (1985)) or CNS (Brunger et al., *Acta Cryst.* D54: 905-921, (1998)).

In order that this invention be more fully understood, the following examples are set forth. These examples are for the purpose of illustration only and are not to be construed as limiting the scope of the invention in any way.

Example 1

Cloning and Expression of ROCK I

Rock I (Swiss-Prot # Q13464) was isolated from a human leukocyte cDNA library (BD Biosciences Clontech, Mountain View, Calif.). The cDNA encoding the ROCK protein limits S6-L553 and S6-R415 were cloned into a baculoviral transfer vector, pBEV10, and expressed in insect cells according to (Chambers et al., *Protein Expression and Purification* 36: 40-47 (2004)). The proteins were engineered to include a hexa-histidine tag ($His_6$) at the N-terminus to facilitate purification.

Example 2

Purification of ROCK I

The protein used for crystallization was first produced by proteolytic cleavage of a larger construct, and later through construction of a DNA expression vector containing sequences corresponding to the desired proteolytic product. The ROCK S6-L553 construct was metal-affinity purified according to (Doran et al., *Biochem J.* 384, 255-262 (2004)). After thrombin cleavage of the His tag, the sample was treated with clostripain (Washington Chemicals) at a ratio of 1:100 (wt/wt) and 10 mM $CaCl_2$ for 3 hours at room temperature followed by overnight incubation at 4° C. This yielded a C-terminally truncated enzyme whose limits were determined to be S6-R415 through a combination of N-terminal sequencing and Matrix assisted laser desorption/ionization time-of flight (MALDI-TOF) mass spectrometry. N-terminal sequencing was performed on an Applied Biosystems Precise Sequencing System using standard methods with the purified protein sample applied directly to a Prosorb (Applied Biosystems) PVDF membrane following the manufacturers instructions. MALDI-TOF mass spectrometry was performed on an Applied Biosystems Voyager-DE STR Biospectrometry Workstation.

The S6-R415 protein was then diluted 10-fold with 20 mM HEPES, pH 7.4, loaded onto a MonoQ HR 5/5 ion-exchange column (Amersham Biosciences), and eluted with a 100-400 mM NaCl gradient over 40 column volumes. The sample was then loaded onto a HiLoad 16/60 Superdex 200 column (Amersham Biosciences) equilibrated with 20 mM HEPES, 200 mM NaCl, 2 mM β-mercaptoethanol, pH 7.4. The main peak was pooled and appeared to be 99% pure as judged by SDS-PAGE analysis. The ROCK S6-L415 construct was purified using an identical procedure except that the clostripain proteolysis step was omitted.

Example 3

Crystallization of ROCK I and ROCK I-Inhibitor Complexes

ROCK crystals were grown by the vapor diffusion method at 18-22° C. Equal volumes of the ROCK S6-L415 protein (14-20 mg/ml protein, 20 mM HEPES pH 7.8, 100 mM NaCl, 2 mM 2-mercaptoethanol) and well solution (3-8% PEG-3350, 100 mM MES buffer pH 5.5, 50 mM $CaCl_2$ and 10 mM DTT) were mixed and suspended over 1 ml of well solution. Crystals also grew using 10-20 mg/ml of ROCK S6-L415 protein mixed with equal volume of well solution containing 2-7% PEG3350, 100 mM HEPES buffer pH 5.3-5.6, 40-50 mM CaCl$_2$, 0-10 mM DTT and 0-5% DMSO. The best diffracting crystals grew using 20 mg/ml of ROCK S6-L415 protein mixed with equal volume of well solution containing 4.5% PEG3350, 100 mM MES buffer pH 5.5, 50 mM CaCl$_2$ and 10 mM DTT. Over four days, the crystals reached a final size of approximately 200 μm. Crystals were harvested and flash-frozen in a solution composed of the well solution with 30% (v/v) glycerol. Inhibitor-complex crystals of ROCK with inhibitors 2, 3, 4 and 5 were made by soaking apo or unliganded crystals with 500 μM compound and 5% DMSO (final concentration) in well solution for 48 hours at room temperature. Rock I-inhibitor complexes were also made by adding the ligand (2 mM) to the protein prior to crystallization.

Example 4

X-Ray Data Collection and Structure Determination

The diffraction data were recorded at Beamline 5.0.2 at the Advanced Light Source (Lawrence Berkeley Laboratories). Intensities were integrated and scaled using the programs DENZO and SCALEPACK (Otwinoski, Z. (1993) *Oscillation data reduction program*. Data Collection and Processing (L. Sawyer, N. W. I., and S. Bailey, Ed.), Warrington, England: SERC Daresbury Laboratory) and CrystalClear (CrystalClear: An Integrated Program for the Collection and Processing of Area Detector Data, R. C., © 1997-2002).

The structures were determined by molecular replacement using homology models based upon c-AMP dependent kinase (PKA). The molecular replacement solution was determined using AMORE (CCP4 (Collaborative Computational Project, N. *Acta Crystallogr. D.* 50: 760-763 (1994); Navaza, *Acta Crystallogr D Biol Crystallogr* 57: 1367-1372 (2001)). The crystals belong to the space group P3$_1$21. The asymmetric unit consists of two monomers which are well ordered and interact with each other. The asymmetric unit also contains the N-terminal region of a third molecule which interacts with a symmetry-related molecule across a two-fold axis. The electron density for this region is quite poor, and the remainder of the molecule (kinase domain) is not visible at all. The protein model was built using QUANTA (Accelrys, San Diego, Calif.) and refined with CNX (Accelrys, San Diego, Calif.; Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T., and Warren, G. L. *Acta Crystallogr D Biol Crystallogr* 54 (Pt 5): 905-921 (1998)). Table 1 summarizes the refinement statistics.

Table 2 lists the atomic structure coordinates in Protein Data Bank (PDB)-like format and header for human ROCK I in complex with inhibitor2, as derived by X-ray diffraction from a crystal of the complex. The structure model includes human ROCK I kinase amino acid residues 6-405 of SEQ ID NO:1 for chain A and residues 5-402 of SEQ ID NO:1 for chain B. Due to the weak electron density, residues 6, 114, 287, and 374 were built in chain A as alanine. Residues 5, 302, and 375 were built in chain B as alanine. SEQ ID NO:4 and SEQ ID NO:5 given in the "SEQRES" section of Tables 2-5 represent the amino acid residues of the structural model for chain A and chain B, respectively.

Table 3 lists the atomic structure coordinates in Protein Data Bank (PDB)-like format and header for human ROCK I in complex with inhibitor3, as derived by X-ray diffraction from a crystal of the complex. The structure model includes human ROCK I kinase amino acid residues 6-405 of SEQ ID NO:1 for chain A and residues 5-402 of SEQ ID NO:1 for chain B. Due to the weak electron density, residues 6, 114, 287, and 374 were built in chain A as alanine. Residues 5, 302, and 375 were built in chain B as alanine.

Table 4 lists the atomic structure coordinates in Protein Data Bank (PDB)-like format and header for human ROCK I in complex with inhibitor4, as derived by X-ray diffraction from a crystal of the complex. The structure model includes human ROCK I kinase amino acid residues 6-405 of SEQ ID NO:1 for chain A and residues 5-402 of SEQ ID NO:1 for chain B. Due to the weak electron density, residues 6, 114, 287, and 374 were built in chain A as alanine. Residues 5, 302, and 375 were built in chain B as alanine.

Table 5 lists the atomic structure coordinates in Protein Data Bank (PDB)-like format and header for human ROCK I in complex with inhibitor5, as derived by X-ray diffraction from a crystal of the complex. The structure model includes human ROCK I kinase amino acid residues 6-405 of SEQ ID NO:1 for chain A and residues 5-402 of SEQ ID NO:1 for chain B. Due to the weak electron density, residues 6, 114, 287, and 374 were built in chain A as alanine. Residues 5, 302, and 375 were built in chain B as alanine.

The following abbreviations are used in Table 2, 3, 4, or 5:

"Atom type" refers to the element whose coordinates are measured. The first letter in the column defines the element.

"Resid" refers to the amino acid residue in the molecular model.

"X, Y, Z" define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in the molecules.

"Mol" refers to a molecule in the asymmetric unit. "A" and "B" refers to chain A and chain B of ROCK I molecule in the asymmetric unit, respectively. "Z" and "Y" represents the inhibitors in the asymmetric unit.

Example 8

Overview of Crystal Structure of ROCK I-Inhibitor Complex

The crystal structure of ROCK I reveals two protein molecules related by a pseudo-twofold rotation (axis parallel to crystallographic threefold). Each monomer consists of three parts: an N-terminal helical domain (residues 5-72), a kinase domain (residues 73-356) and a C-terminal tail (residues 357-405). Helices from each of the monomers interact with each other to form what appears to be a single domain. This region will be referred to hereafter as the dimerization domain. The C-terminal tail of each molecule lies across its own kinase domain and interacts with the dimerization domain.

The kinase domain of ROCK I has a global fold typical of protein serine/threonine kinases, consisting of two lobes linked by a hinge region (FIG. 1). The smaller, N-terminal lobe (residues 73-153) contains a twisted five-stranded antiparallel β-sheet and a single α-helix (called the C-helix). The C-terminal lobe (residues 159-356) is largely α-helical. The ATP binding pocket of the active site is formed by a groove at the interface between these two domains, and is enclosed by the hinge region (residues 154-158), the glycine rich loop (residues 81-91), and the activation loop (residues 216-231).

The ROCK I kinase domain structure was compared to c-AMP dependent kinase (PKA; Protein Data Bank Accession No. 1ATP), the most similar kinase with respect to sequence identity for which the three dimensional structure is known. When secondary structural elements are aligned, a root mean square difference (RMSD) of 1.3 Å for C-α atom positions was observed between ROCK I and PKA (using 220 residues).

Active Site Conformation

It is thought that ROCK I is activated by disrupting interactions between the kinase domain and regulatory elements in the C-terminus, either through rho RhoA binding or cleavage of the C-terminus by caspase. Since the crystallization construct used to determine the ROCK I structure lacked these C-terminal domains, we expected to observe a catalytically competent conformation. In particular, we expected that the residues of the active site would be aligned as in other active kinase structures, and the activation loop would not occlude the peptide substrate binding groove.

The conformation of the activation loop revealed the mechanism for ROCK I constitutive activity in the absence of inhibitory C-terminal domains. Among protein kinases, the conformation of the activation loop varies widely. In inactive kinase conformations, the activation loop often blocks the active site, interfering with peptide and ATP substrate binding. In active kinase conformations, this loop lies over and parallel to helices E and F. While the sequence and conformation of the activation loop vary among active kinases, they all follow roughly the same trajectory.

In ROCK I, the activation loops of the two molecules in the asymmetric unit are very similar (0.3 Å RMSD over main-chain atoms), diverging only at the region between the activation loop and the EF helix (Asp232-Pro238), where each of the two monomers make quite different crystal lattice contacts. In this region, residues in chain B move away from the active site by about 5 Å compared to that observed in the structure of PKA. See Breitenlechner et al., Structure, 11: 1595-1607 (2003). It appears that crystal contact between chain B residues 246-249 account for this different conformation and indicate that these loop regions are likely to be flexible.

Substrate Binding

The ROCK I substrate amino acid consensus sequence for phosphorylation is (Arg/Lys)X(Ser/Thr) or (Arg/Lys)XX(Ser/Thr), where X represents any amino acid. A similar sequence is found in the peptide substrate of the PKA/ATP/peptide complex structure (Protein Data Bank accession no. 1ATP), Arg-Arg-Asn-Ala (SEQ ID NO: 2), where alanine has been substituted for the phosphoreceptor residue. The PKA/peptide and ROCK I structures were superimposed to model the interactions between ROCK I and its substrate. There is a lack of specificity for the residue immediately prior to the Ser/Thr is compatible with the PKA/PKI complex structure (Protein Data Bank accession no. 1ATP), because the Cα-Cβ bond of the residue at this position points away from the active site. Essentially any residue could be accommodated at this position without disrupting peptide binding. In the PKA structure, the two Arg residues before the Ser/Thr each form salt bridges to acidic residues in PKA. The corresponding residues in ROCK I are also acidic, so similar interactions are compatible with the ROCK I structure.

Example 9

ROCK I-Inhibitor Interactions

Common interactions were found between inhibitors 2, 3, and 4 and the ROCK I residues (the thiophene ring of inhibitor3 makes the same contacts as the thiazole in the other compounds) (FIG. 2A). The pyrimidine N accepts a hydrogen bond from the main chain amide N of Met156. The pyrimidine C2 (atom C16) hydrogen is likely to donate a hydrogen bond to the main chain carbonyl of Glu154. The pyrimidine ring is sandwiched between the side chains of Leu205 below (toward C-terminal domain), Ala103 and Met153 above (toward N-terminal domain) the plane of the ring. One edge of the pyrimidine ring packs against the side chains of Ala215, Val137, and Met156, while the other edge packs against the Ile82, Val90, Tyr155, and Phe368 side chains. The thiazole ring packs against the side chains of Ala215, Leu205, Met128, Met153, Val90, Lys105, and against the main chain atoms of Asp216. The carbonyl of the amide bond of the compounds forms a hydrogen bond to the side chain amine of Lys105.

For inhibitor2, the phenyl ring packs against the glycine rich loop (residues 83-90) and the side chain of Lys105. The 3 carbon linker attached to the amide nitrogen (forming the piperadin-2-one) contacts Asp216, Val90, Gly83, and Arg84.

For inhibitor3, the phenyl ring packs against the glycine rich loop (residues 83-90) and the side chain of Lys 105. At the meta position, a solubilizing group is attached (O—($CH_2$)$_3$-piperazine-$CH_3$). The O—($CH_2$)$_3$ linker packs against the side chains of Lys105, Leu107, Phe87, and Phe120, and Ala86. The methyl-piperazine packs against Phe120, Phe87, Gly218, Thr219, Val235, and Ser116. The piperazine is near Asp117, indicating an electrostatic interaction (+ on piperazine, − on Asp).

For inhibitor4, the bromobenzodioxole packs against the glycine-rich loop (residues 83-90) and the side chain of Lys 105. The Br atom packs against the side chain of Val90.

For inhibitor5, the pyrazolo-pyridine forms two hydrogen bonds: to the Met156 main chain NH and Glu154 main chain carbonyl (FIG. 2B). This ring is sandwiched between the side chains of Leu205 below (toward C-terminal domain), and Val90, Ala103 and Met153 above (toward N-terminal domain) the plane of the ring. The pyrazolo-pyridine also contacts the side chains of Ala215, Val137, Met156, Ile82, Tyr155, and Phe368. The pyrazole nitrogen also forms a hydrogen bond to a water molecule, which in turn, interacts with the main chain NH's of Asp216 and Phe217. The ligand amide carbonyl interacts with the side chain of Lys105. The phenyl ring packs against the glycine rich loop (residues 83-90) and the side chain of Lys 105.

Example 10

ROCK I Kinase Assay

A coupled enzyme assay was used to quantify the ADP generated in the kinase reaction with ROCK peptide (KKRN-RTLSV) (SEQ ID NO: 3). See Fox et al., Protein Sci. 7, 2249-55 (1998). The assay was carried out in 100 mM HEPES buffer, pH 7.6, containing 10 mM $MgCl_2$, 2.5 mM PEP, 0.2 mM NADH, 30 mg/mL pyruvate kinase, 10 mg/mL lactate dehydrogenase and 2 mM DTT in a 96-well plate, at 30 2C, on a Molecular Devices Spectromax spectrophotometer at 340 inn. The Rho-kinase concentration was 100 nM in the assay. The inhibitor was dissolved in DMSO and assayed at a final DMSO concentration of 3%. DMSO alone at 3% showed no significant effect on activity. The inhibitor was incubated for 10 minutes at 30° C. with enzyme prior to initiation of the reaction by ATP addition. For Ki determinations, ATP and ROCK peptide concentrations were at the previously determined $K_M$'S for each enzyme construct.

Kinetic data collected for both the full-length ROCK and for all assays using MLC (myosin light chain) as a substrate were acquired using [γ-$^{33}$P]ATP. For radioactive assays using [γ-$^{33}$P] ATP, all samples were assayed in 50 μl of 100 mM HEPES, 10 mM MgCl$_2$, 2 mM DTT and 0.15% (w/v) CHAPS, pH 7.4. Full-length ROCK II assays were done with and without 5 μM GTPγS-RhoA. RhoA was activated with GTPγS to generate the GTPγS-RhoA complex according to the method by Hammond. See *J. Biol. Chem.* 272: 3860-8 (1997). For determination of peptide or protein K$_M$ values, the ATP concentration was 1 mM (2 μCi of [γ-$^{33}$P]ATP per reaction). All reactions were initiated by the addition of ATP. Following an incubation period of 15 minutes, reactions were stopped by addition of 175 μl of 10% trichloroacetic acid (TCA) for protein substrate or 5% phosphoric acid for peptide substrate. TCA stopped reactions were filtered through Whatman GF/F 96-well filter plates (retaining precipitated product) and phosphoric acid stopped reactions were filtered through Whatman p81 filter 96-well filter plates (absorbing the charged peptide). All plates were washed 4 times with corresponding stop solutions followed by 4 washes of methanol, then 200 μl of scintillant was added to all wells and the plates were counted in a Packard 96-well plate gamma counter. Kinetic constants were determined by nonlinear least-squares analysis using the program GraphPad Prism (GraphPad Software, San Diego, Calif.).

While we have described a number of embodiments of this invention, it is apparent that our basic constructions may be altered to provide other embodiments which utilize the products, processes and methods of this invention.

TABLE 1

Data Collection and Refinement Statistics

| Data set | Inhibitor3 | Inhibitor2 | Inhibitor5 | Inhibitor4 |
|---|---|---|---|---|
| Data collection | | | | |
| X-ray source | APS | ALS | ALS | ALS |
| Space group | P3$_1$21 | P3$_1$21 | P3$_1$21 | P3$_1$21 |
| Unit cell parameters (Å) | a = b = 180.7<br>c = 90.8 | a = b = 181.9<br>c = 91.3 | a = b = 181.5<br>c = 91.1 | a = b = 181.7<br>c = 90.6 |
| Resolution (Å) | 20.0 – 2.95 | 20.0 – 3.1 | 20.0 – 3.1 | 20.0 – 3.4 |
| Redundancy | 5.8 | 7.0 | 6.2 | 5.2 |
| Completeness (%)* | 100 (100) | 93.7 (95.4) | 99.2 (99.7) | 77.2 (80.4) |
| R$_{merge}$* | 0.17 (0.43) | 0.06 (0.37) | 0.11 (0.37) | 0.12 (0.38) |
| <I/σ>* | 6.8 (2.4) | 18.9 (4.7) | 6.5 (2.0) | 14.9 (5.4) |
| Refinement | | | | |
| Reflections used | 34817 | 28159 | 28551 | 16892 |
| Test reflections | 1738 | 1430 | 1440 | 881 |
| R-factor | 0.278 | 0.244 | 0.262 | 0.247 |
| Free R-factor | 0.310 | 0.283 | 0.278 | 0.276 |
| RMS deviations | | | | |
| Bond lengths (Å) | 0.011 | 0.007 | 0.006 | 0.006 |
| Bond angles (°) | 1.6 | 1.2 | 1.2 | 1.1 |
| Dihedral angles(°) | 22.2 | 22.2 | 21.9 | 21.9 |

*Values for the highest resolution shell are shown in parentheses.

R$_{merge}$ = Σ$_{hkl}$ Σ$_i$|I(hkl)$_i$ − <I(hkl)>|/Σ$_{hkl}$ Σ$_i$<I(hkl)$_i$> over i observations of reflection hkl.

R-factor = Σ||F$_{obs}$| − |F$_{calc}$||/Σ|F$_{obs}$| where F$_{obs}$ and F$_{calc}$ are the observed and calculated structure factors, respectively. Free R-factor is calculated from a randomly chosen subset of reflections not used for refinement. The same reflection subset was used for all four data sets.

Lengthy table referenced here

US07655446-20100202-T00001

Please refer to the end of the specification for access instructions.

Lengthy table referenced here

US07655446-20100202-T00002

Please refer to the end of the specification for access instructions.

Lengthy table referenced here

US07655446-20100202-T00003

Please refer to the end of the specification for access instructions.

Lengthy table referenced here

US07655446-20100202-T00004

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US07655446B2). An electronic copy of the table will also be available from the USPTO upon request and payment of the fee set forth in 37 CFR 1.19(b)(3).

We claim:

1. A crystal comprising a human Rho-kinase I kinase domain, wherein said domain consists of amino acids 6-415 of SEQ ID NO: 1, and wherein said crystal is characterized with space group $P3_121$ and unit cell parameters of a=b=182 Å±3 Å, c=92 Å±3 Å, $\alpha=\beta=90°$; and $\gamma=120°$.

2. A crystal comprising a human Rho-kinase I kinase domain, said domain being in complex with any one of 3-phenyl-1-(4-(pyridin-4-yl)thiazol-2-yl)piperidin-2-one, 2-(3-(3-(4-methylpiperazin-1-yl)propoxy)phenyl)-N-(4-(pyridin-4-yl)thiophen-2-yl)acetamide, 2-(5-bromobenzo[d][1,3]dioxol-6-yl)-N-(4-(pyridin-4-yl)thiazol-2-yl)acetamide, or N-((S)-2-hydroxy-1-phenylethyl)-4-(1H-pyrazolo[3,4-b]pyridin-3-yl)-1H-pyrrole-2-carboxamide wherein said domain consists of amino acids 6-415 of SEQ ID NO: 1, and wherein said crystal is characterized with space group $P3_121$ and unit cell parameters of a=b=182 Å±3 Å, c=92 Å±3 Å, $\alpha=\beta=90°$; and $\gamma=120°$.

* * * * *